US012806237B2

(12) United States Patent
Ohno et al.

(10) Patent No.: US 12,806,237 B2
(45) Date of Patent: Nov. 24, 2026

(54) METHODS AND COMPOSITIONS FOR INTESTINAL INFLAMMATION

(71) Applicant: THE REGENTS OF THE UNIVERSITY OF MICHIGAN, Ann Arbor, MI (US)

(72) Inventors: Masashi Ohno, Ann Arbor, MI (US); Gabriel Nunez, Ann Arbor, MI (US); Naohiro Inohara, Ann Arbor, MI (US); Mizuho Hasegawa, Ann Arbor, MI (US)

(73) Assignee: The Regents of the University of Michigan, Ann, Arbor, MI (US)

( * ) Notice: Subject to any disclaimer, the term of this patent is extended or adjusted under 35 U.S.C. 154(b) by 677 days.

(21) Appl. No.: 18/028,398

(22) PCT Filed: Sep. 28, 2021

(86) PCT No.: PCT/US2021/052266
§ 371 (c)(1),
(2) Date: Mar. 24, 2023

(87) PCT Pub. No.: WO2022/067219
PCT Pub. Date: Mar. 31, 2022

(65) Prior Publication Data

US 2023/0364162 A1 Nov. 16, 2023

Related U.S. Application Data

(60) Provisional application No. 63/084,204, filed on Sep. 28, 2020.

(51) Int. Cl.
*A61K 35/741* (2015.01)
*A61P 1/04* (2006.01)
*C12Q 1/689* (2018.01)

(52) U.S. Cl.
CPC .............. *A61K 35/741* (2013.01); *A61P 1/04* (2018.01); *C12Q 1/689* (2013.01)

(58) Field of Classification Search
CPC .......... A61K 35/741; A61P 1/04; C12Q 1/689
See application file for complete search history.

(56) References Cited

U.S. PATENT DOCUMENTS

| | | | | |
|---|---|---|---|---|
| 2015/0164984 | A1 | 6/2015 | Walker et al. | |
| 2016/0015781 | A1 | 1/2016 | Olschlager et al. | |
| 2017/0087237 | A1 | 3/2017 | Gunn et al. | |
| 2020/0069747 | A1* | 3/2020 | Gibson | A23K 10/18 |
| 2020/0123207 | A1 | 4/2020 | Ittig et al. | |
| 2020/0270569 | A1 | 8/2020 | Bucci et al. | |

FOREIGN PATENT DOCUMENTS

| | | |
|---|---|---|
| WO | WO 2011/113003 | 9/2011 |
| WO | WO 2013/075185 | 5/2013 |
| WO | WO 2016/033439 | 3/2016 |
| WO | WO 2017/136792 | 8/2017 |
| WO | WO 2020/215055 | 10/2020 |

OTHER PUBLICATIONS

Dreux, Nicolas, et al. "Point mutations in FimH adhesin of Crohn's disease-associated adherent-invasive *Escherichia coli* enhance intestinal inflammatory response." PLoS pathogens 9.1 (2013): e1003141. (Year: 2013).*

CDC, retrieved from https://www.cdc.gov/inflammatory-bowel-disease/causes/index.html#:~:text=More%20than%20200%20genetic%20mutations,IBD%20can%20also%20increase%20risk. on Dec. 16, 2025. (Year: 2024).*

Shanahan, Fergus, Tarini S. Ghosh, and Paul W. O'Toole. "The healthy microbiome—what is the definition of a healthy gut microbiome?." Gastroenterology 160.2 (2021): 483-494. (Year: 2021).*

Nash, John HE, et al. "Genome sequence of adherent-invasive *Escherichia coli* and comparative genomic analysis with other *E. coli* pathotypes." BMC genomics 11.1 (2010): 667. (Year: 2010).*

Marks, Daniel JB, et al. "Crohn's disease: an immune deficiency state." Clinical reviews in allergy & immunology 38.1 (2010): 20-31. (Year: 2010).*

Zimmermann-Nielsen, E., et al. "Complement activation in plasma before and after infliximab treatment in Crohn disease." Scandinavian journal of gastroenterology 38.10 (2003): 1050-1054. (Year: 2003).*

Prantera, C., et al. "An antibiotic regimen for the treatment of active Crohn's disease: a randomized, controlled clinical trial of metronidazole plus ciprofloxacin." The American journal of gastroenterology 91.2 (1996): 328-332. (Year: 1996).*

Zuo, Jiakun, et al. "The role of the wzy gene in lipopolysaccharide biosynthesis and pathogenesis of avian pathogenic *Escherichia coli*." Microbial pathogenesis 127 (2019): 296-303. (Year: 2019).*

Datsenko, Kirill A., and Barry L. Wanner. "One-step inactivation of chromosomal genes in *Escherichia coli* K-12 using PCR products." Proceedings of the National Academy of Sciences 97.12 (2000): 6640-6645. (Year: 2000).*

International Search Report and Written Opinion for PCT/US2021/052266. Mailed Jan. 6, 2022. 25 pages.

Abreu et al., How *Escherichia coli* Circumvent Complement-Mediated Killing. Front Immunol. Apr. 20, 2017:8:452. 6 pages.

Anderson et al., Capsule Production and Glucose Metabolism Dictate Fitness during Serratia marcescens Bacteremia. mBio. May 23, 2017;8(3):e00740-17.

(Continued)

*Primary Examiner* — Robert J Yamasaki
*Assistant Examiner* — Trevor Kane
(74) *Attorney, Agent, or Firm* — Kirk J. Hogan; Casimir Jones, S.C.

(57) ABSTRACT

Provided herein are compositions and methods for the management of intestinal inflammation. In particular, compositions comprising modified adherent-invasive *E. coli* (AIEC) are administered to human and/or animal subjects to treat, prevent or decrease susceptibility to intestinal inflammation.

10 Claims, 14 Drawing Sheets

Specification includes a Sequence Listing.

(56) References Cited

OTHER PUBLICATIONS

Baumgart et al., Culture independent analysis of ileal mucosa reveals a selective increase in invasive *Escherichia coli* of novel phylogeny relative to depletion of Clostridiales in Crohn's disease involving the ileum. ISME J. Sep. 2007;1(5):403-18.
Bernstein. Treatment of IBD: where we are and where we are going. Am J Gastroenterol. Jan. 2015;110(1):114-26.
Bringer et al., HtrA stress protein is involved in intramacrophagic replication of adherent and invasive *Escherichia coli* strain LF82 isolated from a patient with Crohn's disease. Infect Immun. Feb. 2005;73(2):712-21.
Buckles et al., Role of the K2 capsule in *Escherichia coli* urinary tract infection and serum resistance. J Infect Dis. Jun. 1, 2009;199(11):1689-97.
Castellanos et al., Microbiota-Induced TNF-like Ligand 1A Drives Group 3 Innate Lymphoid Cell-Mediated Barrier Protection and Intestinal T Cell Activation during Colitis. Immunity. Dec. 18, 2018;49(6):1077-1089.e5.
Charles et al., A chromosomally encoded two-component sensory transduction system is required for virulence of Agrobacterium tumefaciens. J Bacteriol. Oct. 1993;175(20):6614-25.
Chassaing et al., Fecal lipocalin 2, a sensitive and broadly dynamic non-invasive biomarker for intestinal inflammation. PLoS One. 2012;7(9):e44328. 8 pages.
Clermont et al., Rapid and simple determination of the *Escherichia coli* phylogenetic group. Appl Environ Microbiol. Oct. 2000;66(10):4555-8.
Comstock et al., Bacterial glycans: key mediators of diverse host immune responses. Cell. Sep. 8, 2006;126(5):847-50.
Darfeuille-Michaud et al., High prevalence of adherent-invasive *Escherichia coli* associated with ileal mucosa in Crohn's disease. Gastroenterology. Aug. 2004;127(2):412-21.
Datsenko et al., One-step inactivation of chromosomal genes in *Escherichia coli* K-12 using PCR products. Proc Natl Acad Sci U S A. Jun. 6, 2000;97(12):6640-5.
De Vries et al., Genome-wide fitness analyses of the foodborne pathogen Campylobacter jejuni in in vitro and in vivo models. Sci Rep. Apr. 28, 2017;7(1):1251. 17 pages.
Demarre et al., The Crohn's disease-associated *Escherichia coli* strain LF82 relies on SOS and stringent responses to survive, multiply and tolerate antibiotics within macrophages. PLoS Pathog. Nov. 14, 2019;15(11):e1008123. 25 pages.
Dreux et al., Point mutations in FimH adhesin of Crohn's disease-associated adherent-invasive *Escherichia coli* enhance intestinal inflammatory response. PLoS Pathog. Jan. 2013;9(1):e1003141. 17 pages.
Fang et al., Probiotic *Escherichia coli* inhibits biofilm formation of pathogenic *E. coli* via extracellular activity of DegP. Sci Rep. Mar. 21, 2018;8(1):4939. 12 pages.
Franchi et al., Sensing and reacting to microbes through the inflammasomes. Nat Immunol. Mar. 19, 2012;13(4):325-32.
Frank et al., Molecular-phylogenetic characterization of microbial community imbalances in human inflammatory bowel diseases. Proc Natl Acad Sci U S A. Aug. 21, 2007;104(34):13780-5.
Garrity et al., The Taxonomic Outline of Bacteria and Archaea. TOBA Release 7.7, Mar. 2007. Michigan State University Board of Trustees. 141 pages.
Geremia et al., IL-23-responsive innate lymphoid cells are increased in inflammatory bowel disease. J Exp Med. Jun. 6, 2011;208(6):1127-33.
Grozdanov et al., A single nucleotide exchange in the wzy gene is responsible for the semirough O6 lipopolysaccharide phenotype and serum sensitivity of *Escherichia coli* strain Nissle 1917. J Bacteriol. Nov. 2002;184(21):5912-25.
Guo et al., Molecular analysis of the O-antigen gene cluster of *Escherichia coli* O86:B7 and characterization of the chain length determinant gene (wzz). Appl Environ Microbiol. Dec. 2005;71(12):7995-8001.
Guo et al., Taxonomic precision of different hypervariable regions of 16S rRNA gene and annotation methods for functional bacterial groups in biological wastewater treatment. PLoS One. Oct. 16, 2013;8(10):e76185. 11 pages.
Hamady et al., Microbial community profiling for human microbiome projects: Tools, techniques, and challenges. Genome Res. 2009; 19: 1141-1152.
Hancock et al., Probiotic *Escherichia coli* strain Nissle 1917 outcompetes intestinal pathogens during biofilm formation. J Med Microbiol. Apr. 2010;59(Pt 4):392-399.
Hasegawa et al., Interleukin-22 regulates the complement system to promote resistance against pathobionts after pathogen-induced intestinal damage. Immunity. Oct. 16, 2014;41(4):620-32.
Hasegawa et al., Nucleotide-binding oligomerization domain 1 mediates recognition of Clostridium difficile and induces neutrophil recruitment and protection against the pathogen. J Immunol. Apr. 15, 2011;186(8):4872-80.
Hasegawa et al., Protective role of commensals against Clostridium difficile infection via an IL-1β-mediated positive-feedback loop. J Immunol. Sep. 15, 2012;189(6):3085-91.
Hayashi et al., A single strain of Clostridium butyricum induces intestinal IL-10-producing macrophages to suppress acute experimental colitis in mice. Cell Host Microbe. Jun. 12, 2013;13(6):711-22.
Kaser et al., Inflammatory bowel disease. Annu Rev Immunol. 2010:28:573-621.
Kenyon et al., The Wzy O-antigen polymerase of Yersinia pseudotuberculosis O:2a has a dependence on the Wzz chain-length determinant for efficient polymerization. FEMS Microbiol Lett. Dec. 2013;349(2):163-70.
Kozich et al., Development of a dual-index sequencing strategy and curation pipeline for analyzing amplicon sequence data on the MiSeq Illumina sequencing platform. Appl Environ Microbiol. Sep. 2013;79(17):5112-20.
Kruis et al., Maintaining remission of ulcerative colitis with the probiotic *Escherichia coli* Nissle 1917 is as effective as with standard mesalazine. Gut. Nov. 2004;53(11):1617-23.
Lebeer et al., Host interactions of probiotic bacterial surface molecules: comparison with commensals and pathogens. Nat Rev Microbiol. Mar. 2010;8(3):171-84.
Lee et al., Characteristics and pathogenic role of adherent-invasive *Escherichia coli* in inflammatory bowel disease: Potential impact on clinical outcomes. PLoS One. Apr. 29, 2019;14(4):e0216165.
Liu et al., Genetics and Pathogenesis of Inflammatory Bowel Disease. Annu Rev Pathol. May 23, 2016:11:127-48.
Massip et al., Deciphering the interplay between the genotoxic and probiotic activities of *Escherichia coli* Nissle 1917. PLoS Pathog. Sep. 23, 2019;15(9):e1008029. 1-24.
Miajlovic et al., Bacterial self-defence: how *Escherichia coli* evades serum killing. FEMS Microbiol Lett. May 2014;354(1):1-9.
Moriel et al., *Escherichia coli*: great diversity around a common core. mBio. Jun. 5, 2012;3(3):e00118-12.
Nedialkova et al., Inflammation fuels colicin Ib-dependent competition of *Salmonella serovar* Typhimurium and *E. coli* in enterobacterial blooms. PLoS Pathog. Jan. 2014;10(1):e1003844. 1-15 pages.
Newcombe et al., On the nonadaptive nature of change to full streptomycin resistance in *Escherichia coli*. J Bacteriol. Nov. 1951;62(5):539-44.
Oberholzer et al., Decomplementation with cobra venom factor prolongs survival of xenografted islets in a rat to mouse model. Immunology. May 1999;97(1):173-80.
Ohno et al., Lipopolysaccharide O structure of adherent and invasive *Escherichia coli* regulates intestinal inflammation via complement C3. PLoS Pathog. Oct. 7, 2020;16(10):e1008928. 22 pages.
Page et al., Roary: rapid large-scale prokaryote pan genome analysis. Bioinformatics. Nov. 15, 2015;31(22):3691-3.
Palmela et al., Adherent-invasive *Escherichia coli* in inflammatory bowel disease. Gut. Mar. 2018;67(3):574-587.
Patzer et al., The colicin G, H and X determinants encode microcins M and H47, which might utilize the catecholate siderophore receptors FepA, Cir, Fiu and IroN. Microbiology (Reading). Sep. 2003;149(Pt 9):2557-2570.

(56) References Cited

OTHER PUBLICATIONS

Pearson. Rapid and sensitive sequence comparison with FASTP and FASTA. Methods Enzymol. 1990:183:63-98.

Pickert et al., STAT3 links IL-22 signaling in intestinal epithelial cells to mucosal wound healing. J Exp Med. Jul. 6, 2009;206(7):1465-72.

Pitout. Extraintestinal Pathogenic *Escherichia coli*: A Combination of Virulence with Antibiotic Resistance. Front Microbiol. Jan. 19, 2012:3:9. 7 pages.

Poolman et al., Extraintestinal Pathogenic *Escherichia coli*, a Common Human Pathogen: Challenges for Vaccine Development and Progress in the Field. J Infect Dis. Jan. 1, 2016;213(1):6-13.

Porter et al., The Critical Roles of Polysaccharides in Gut Microbial Ecology and Physiology. Annu Rev Microbiol. Sep. 8, 2017:71:349-369.

Remington's Pharmaceutical Sciences, Mack Publ. Co., Easton, PA. 1985. TOC only. 4 pages.

Sabat et al., Therapeutic opportunities of the IL-22-IL-22R1 system. Nat Rev Drug Discov. Jan. 2014;13(1):21-38.

Sachdeva et al., *E. coli* Group 1 Capsular Polysaccharide Exportation Nanomachinary as a Plausible Antivirulence Target in the Perspective of Emerging Antimicrobial Resistance. Front Microbiol. Jan. 31, 2017:8:70. 19 pages.

Sakamoto et al., IL-22 Controls Iron-Dependent Nutritional Immunity Against Systemic Bacterial Infections. Sci Immunol. Feb. 2017;2(8):eaai8371. 1-9.

Sarkar et al., Role of capsule and O antigen in the virulence of uropathogenic *Escherichia coli*. PLoS One. Apr. 10, 2014;9(4):e94786. 1-11.

Sassone-Corsi et al., Microcins mediate competition among Enterobacteriaceae in the inflamed gut. Nature. Dec. 8, 2016;540(7632):280-283.

Schloss et al., Introducing mothur: open-source, platform-independent, community-supported software for describing and comparing microbial communities. Appl Environ Microbiol. Dec. 2009;75(23):7537-41.

Schmitz et al., Murine Adherent and Invasive *E. coli* Induces Chronic Inflammation and Immune Responses in the Small and Large Intestines of Monoassociated IL-10-/- Mice Independent of Long Polar Fimbriae Adhesin A. Inflamm Bowel Dis. Apr. 11, 2019;25(5):875-885.

Seemann. Prokka: rapid prokaryotic genome annotation. Bioinformatics. Jul. 15, 2014;30(14):2068-9.

Seo et al., Distinct Commensals Induce Interleukin-1α via NLRP3 Inflammasome in Inflammatory Monocytes to Promote Intestinal Inflammation in Response to Injury. Immunity. Apr. 21, 2015;42(4):744-55.

Shaler et al., The Unique Lifestyle of Crohn's Disease-Associated Adherent-Invasive *Escherichia coli*. J Mol Biol. Jul. 26, 2019;431(16):2970-2981.

Soergel et al., Selection of primers for optimal taxonomic classification of environmental 16S rRNA gene sequences. ISME J. Jul. 2012;6(7):1440-4.

Sorbara et al., Complement C3 Drives Autophagy-Dependent Restriction of Cyto-invasive Bacteria. Cell Host Microbe. May 9, 2018;23(5):644-652.e5.

Sunderhauf et al., Regulation of epithelial cell expressed C3 in the intestine—Relevance for the pathophysiology of inflammatory bowel disease? Mol Immunol. Oct. 2017:90:227-238.

Whitfield. Biosynthesis and assembly of capsular polysaccharides in *Escherichia coli*. Annu Rev Biochem. 2006:75:39-68.

Woese et al., Towards a natural system of organisms: proposal for the domains Archaea, Bacteria, and Eucarya. Proc Natl Acad Sci U S A. Jun. 1990;87(12):4576-9.

Woodward et al., In vitro bacterial polysaccharide biosynthesis: defining the functions of Wzy and Wzz. Nat Chem Biol. Jun. 2010;6(6):418-23.

Zerbino et al., Velvet: algorithms for de novo short read assembly using de Bruijn graphs. Genome Res. May 2008;18(5):821-9.

Zuo et al., The role of the wzy gene in lipopolysaccharide biosynthesis and pathogenesis of avian pathogenic *Escherichia coli*. Microb Pathog. Feb. 2019:127:296-303.

* cited by examiner

B

C

METHODS AND COMPOSITIONS FOR INTESTINAL INFLAMMATION

This application is a national phase application under 35 U.S.C. § 371 of PCT International Application No.PCT/US2021/052266, filed on Sep. 28, 2021, which claims priority to U.S. provisional patent application Ser. No. 63/084,204 filed Sep. 28, 2020, which is incorporated herein by reference in its entirety.

SEQUENCE LISTING

Incorporated by reference in its entirety herein is a computer-readable nucleotide/amino acid sequence listing submitted concurrently herewith and identified as follows: One 6,752 bytes Byte ASCII (Text) file named "38772-252 SEQUENCE LISTING ST25," created on Mar. 24, 2023.

FIELD

Provided herein are compositions and methods for the management of intestinal inflammation. In particular, compositions comprising modified adherent-invasive *E. coli* (AIEC) are administered to human and/or animal subjects to treat, prevent or decrease susceptibility to intestinal inflammation.

BACKGROUND

Intestinal inflammation, including colitis and inflammatory bowel disease (IBD), is caused by genetic and environmental factors that alter intestinal homeostasis. Many IBD-associated genetic loci regulate the recognition and killing of bacteria as well as the function of immune cells. In patients with IBD and colitis, there is an alteration in the composition and structure of the gut microbiota which includes a bloom of AIEC. Colonization by certain AIEC strains promotes the induction of colitis. Accordingly, compositions and methods are needed for the management of AIEC-associated intestinal inflammation, colitis and IBD.

SUMMARY

In some embodiments, provided herein are methods, kits, and compositions for administering therapeutic modified AIEC bacteria to a subject to promote healthy microbiota and thereby prevent and/or decrease susceptibility to intestinal inflammation, colitis and IBD.

In some embodiments, the present invention provides a method of preventing, treating or ameliorating intestinal inflammation in a subject, comprising administering to the subject a therapeutically effective amount of a modified adherent-invasive *E. coli* (AIEC) and a pharmaceutically acceptable carrier. In certain embodiments, the modified AIEC is a mutant AIEC. In particular embodiments, the mutant AIEC comprises a mutant lipopolysaccharide O polymerase (wzy) gene. In other embodiments, the mutant AIEC comprises mutations in the lipopolysaccharide O synthetic pathway, and/or in the lipopolysaccharide O metabolic pathway. In further embodiments, the mutant wzy AIEC comprises a deleted wzy gene. In other embodiments, the mutant AIEC has greater sensitivity to the complement system than a non-mutant AIEC bacteria. In additional embodiments, the mutant AIEC has greater susceptibility to engulfment and/or killing by phagocytes than a non-mutant AIEC while retaining its ability to outcompete non-mutant AIEC and enteropathogenic bacteria. In given embodiments, the intestinal inflammation is colitis, chemically-induced colitis, antibiotically-induced colitis, irritable bowel disease, inflammatory bowel disease, Crohn's disease, and/or ulcerative colitis. In specific embodiments, the administering is oral, rectal and/or parenteral administering. In still further embodiments, the subject is immunocompromised. In still other embodiments, the modified AIEC is administered in combination with an antibiotic drug, an anti-diarrheal drug, a laxative drug, a vitamin, a non-steroidal anti-inflammatory drug, a steroidal anti-inflammatory drug, an immune suppressor drug, and/or a biologic therapy. In one embodiment, the modified AIEC is administered in combination with a complement C3 agonist, a colicin antagonist, and/or a C3 inhibitor. In some embodiments, the administering is administering before, during or after surgery. In particular embodiments, the subject has abnormal gut microbiota. In certain embodiments, the subject has pathogenic gut microbiota. In further embodiments, the subject has a gut microbiota that differs from the normal microbiota in one or both of membership or relative abundance of one or more members of the gut microbiota. In additional embodiments, the subject has been previously treated with antibiotics.

In some embodiments, the present invention comprises testing the subject for the presence, absence, or amount of AIEC in the gut microbiota. In certain embodiments, the testing is testing the subject for an abnormal gut microbiota. In other embodiments, the testing is testing the subject for a pathogenic gut microbiota. In some embodiments, the testing comprises use of a labeled probe, nucleic acid amplification, or nucleic acid sequencing or detection of proteins or cellular components by specific binding partners (e.g., antibodies, fragments thereof, etc.).

In some embodiments, the present invention provides a pharmaceutical composition comprising modified AIEC and a pharmaceutically acceptable carrier. In certain embodiments, the composition comprises an effective amount of a modified AIEC. In particular embodiments, the composition is formulated for administration to a human. In other embodiments, the modified AIEC is alive. In still further embodiments, the composition is formulated for oral administration. In still other embodiments, the composition is, formulated for rectal administration. In some embodiments, the pharmaceutical composition is a nutraceutical or a food product.

In some embodiments, the present invention provides a kit comprising a pharmaceutical composition comprising an effective amount of a modified AIEC.

In some embodiments, the present invention provides use of a composition comprising a modified AIEC to treat a subject.

In some embodiments, the present invention provides use of a modified AIEC to manufacture a medicament for administration to a subject.

In some embodiments, the present invention provides use of a composition comprising a modified AIEC to treat or prevent intestinal inflammation in a subject.

In some embodiments, the present invention provides a system for treating intestinal inflammation in a subject, the system comprising: a) a composition comprising a modified AIEC formulated for administration to the subject; and b) a reagent for testing the membership or relative abundance of one or more members of the gut microbiota of the subject. In certain embodiments, the reagent comprises a labeled oligonucleotide probe. In other embodiments, the reagent comprises an amplification oligonucleotide. In some embodiments, the reagent comprising a biomarker-specific binding agent (e.g., antibody, etc.). In particular embodiments, the reagent provides a test for the presence, absence, or level of AIEC in the gut microbiota of the subject.

In some embodiments, the present invention provides a kit for treating intestinal inflammation in a subject, comprising: a) a composition comprising a modified AIEC formulated for administration to the subject; and b) a reagent for testing the membership or relative abundance of one or more members of the gut microbiota of the subject. In other embodiments, the reagent comprises an amplification oligonucleotide. In particular embodiments, the reagent provides a test for the presence, absence, or level of AIEC in the gut microbiota of the subject.

The technology provided herein relates to compositions (e.g., pharmaceutical compositions), methods, kits, and systems for the inhibition of intestinal inflammation (e.g., in a subject, e.g., a human, an animal (e.g., a livestock animal), etc.). In particular, compositions comprising modified AIEC bacteria are administered to human and/or animal subjects to prevent or decrease susceptibility to intestinal inflammation. Modified AIEC bacteria may be administered in any suitable state, for example, live (e.g., vegetative), freeze-dried, etc. Accordingly, provided herein are technologies related to a method of preventing intestinal inflammation in a subject. In some embodiments, the technology provides a method comprising administering a composition comprising modified AIEC to the subject. In some embodiments, methods comprise administering a composition comprising at least $10^4$ colony forming units (CFU) (e.g., at least $1\times10^4$ CFU, $2\times10^4$ CFU, $5\times10^4$ CFU, $1\times10^5$ CFU, $2\times10^5$ CFU, $5\times10^5$ CFU, $1\times10^6$ CFU, $2\times10^6$ CFU, $5\times10^6$ CFU, $1\times10^7$ CFU, $2\times10^7$ CFU, $5\times10^7$ CFU, $1\times10^8$ CFU, $2\times10^8$ CFU, $5\times10^8$ CFU, $1\times10^9$ CFU, $2\times10^9$ CFU, $5\times10^9$ CFU, $1\times10^{10}$ CFU, $2\times10^{10}$ CFU, $5\times10^{10}$ CFU, $1\times10^{11}$ CFU, $2\times10^{11}$ CFU, $5\times10^{11}$ CFU, $1\times10^{12}$ CFU, $2\times10^{12}$ CFU, $5\times10^{12}$ CFU, or more or ranges therebetween) of modified AIEC.

Methods are provided for the treatment of subjects in need of treatment with modified AIEC bacteria. For example, in some embodiments, methods comprise treating a subject having or at risk for having an intestinal inflammation. In some embodiments, methods comprise treating a subject who has an abnormal gut microbiota or a pathogenic gut microbiota, e.g., methods comprise administering a composition comprising modified AIEC to a subject who has an abnormal gut microbiota or a pathogenic gut microbiota. In other embodiments, methods comprise treating a subject who has a gut microbiota that differs from the normal microbiota in one or both of membership or relative abundance of one or more members of the gut microbiota, e.g., methods comprise administering a composition comprising modified AIEC to a subject who has a gut microbiota that differs from the normal microbiota in one or both of membership or relative abundance of one or more members of the gut microbiota. In specific embodiments, the technology relates to methods comprising treating a subject that has a gut microbiota that differs from the normal microbiota in the membership or relative abundance AIEC, e.g., methods comprising administering a composition comprising modified AIEC to a subject who has a gut microbiota that differs from the normal microbiota in the membership or relative abundance of AIEC bacteria.

The technology is not limited in the types or classes of subjects or patients that are treated and/or that are administered the compositions comprising modified AIEC bacteria. For example, in some embodiments the subject is a human. The technology is applicable to subjects and patients that are nonhuman, e.g., mammals, birds, etc., including but not limited to livestock animals, domesticated animals, animals in captivity, etc.

In some embodiments, the subject is a juvenile, adult, or elderly subject.

In some embodiments, the subject has an abnormal or pathogenic gut microbiota due to having previously been treated with antibiotics. In other embodiments, the subject has an abnormal or pathogenic gut microbiota due to current treatment with antibiotics. In given embodiments, the subject is considered to be at risk of having an abnormal or pathogenic gut microbiota due to future treatment with antibiotics. In some embodiments, the subject has undergone a stem cell transplant or will have a stem cell transplant in the future.

The technology is not limited in the type or route if administration. In some embodiments, the type or route of administration provides a composition comprising modified AIEC to the subject's gastrointestinal tract. For example, in some embodiments the composition is administered orally, and in some embodiments the composition is administered rectally. In other embodiments, a composition comprising modified AIEC is administered by fecal microbiota transfer. In certain embodiments, the composition comprising modified AIEC administered by fecal microbiota transfer is administered with bacteria that are not modified AIEC.

In some embodiments, the technology comprises testing a subject or a patient. For example, some embodiments comprise testing the subject for the presence, absence, or amount AIEC in the gut microbiota. Other embodiments comprise testing the subject for an intestinal inflammation. Certain embodiments comprise testing the subject for an abnormal gut microbiota. Particular embodiments comprise testing the subject for a pathogenic gut microbiota. The technology provides methods in which a subject or a patient is tested before and/or after administration of a composition comprising modified AIEC to the subject or patient. In further embodiments, the testing informs the dose amount, dose schedule, and/or CFU of modified AIEC in the composition that is administered to the subject or patient. Additional embodiments comprise administration of a composition comprising modified AIEC to the subject or patient, testing the subject or patient, and a second administration of a composition comprising modified AIEC to the subject. The first and second administrations and/or compositions may be the same or different, e.g., same or different in dose, amount, route, composition, specific strain of modified AIEC, CFU of modified AIEC, etc.

Some embodiments herein include testing the subject or patient for intestinal inflammation, abnormal gut microbiota, pathogenic microbiota, or presence, absence, number, or relative abundance of AIEC in the gut microbiota. In certain embodiments, such testing comprises analysis of a biomarker such as a metabolite, a nucleic acid, a polypeptide, a sugar, a lipid, an indication, a symptom, etc. For example, in some embodiments the technology comprises testing using a labeled probe, a nucleic acid test (NAT), a nucleic acid amplification test (NAAT), a nucleic acid amplification technology (e.g., polymerase chain reaction (e.g., PCR, real-time PCR, probe hydrolysis PCR, reverse transcription PCR), isothermal amplification (e.g., nucleic acid sequence-based amplification (NASBA)), a ligase chain reaction, or a transcription mediated amplification, etc.), or nucleic acid sequencing (e.g., Sanger sequencing or next-gen (e.g., second generation, third generation, etc.) sequencing methods including, e.g., sequencing-by-synthesis, single molecule sequencing, nanopore, Ion Torrent, etc.).

Some embodiments comprise a second testing of the subject or patient, which may be the same or different from the first testing of the patient. The second testing may comprise testing the subject or patient for the presence, absence, or amount of AIEC in the gut microbiota, testing the subject for an intestinal inflammation, testing the subject for an abnormal gut microbiota; and/or testing the subject for a pathogenic gut microbiota. In some embodiments, the second testing occurs after administration of a composition comprising modified AIEC to the subject. In certain embodiments, the second testing indicates that the administration of the composition comprising modified AIEC to the subject is an effective treatment. In other embodiments, the second testing indicates that the administration of the composition comprising modified AIEC to the subject was an ineffective treatment. In further embodiments, the dose amount, dose schedule, and/or type or CFU of modified AIEC in the composition is changed for subsequent administrations to the subject or patient based on the results of the test.

In some embodiments, methods comprise administering to a subject or patient a composition comprising modified AIEC and a non-AIEC probiotic component, or a prebiotic component.

The technology also comprises, in some embodiments, pharmaceutical compositions comprising modified AIEC and a pharmaceutically acceptable carrier. In some embodiments, the pharmaceutical composition comprises an effective amount of modified AIEC. Also, in some embodiments, the pharmaceutical composition comprises additional components, e.g., in some embodiments the pharmaceutical composition comprises a non-AIEC probiotic or a prebiotic.

Non-limiting examples of prebiotics useful in the compositions and methods herein include xylose, arabinose, ribose, galactose, rhamnose, cellobiose, fructose, lactose, salicin, sucrose, glucose, esculin, tween 80, trehalose, maltose, mannose, melibiose, raffinose, fructooligosaccharides (e.g., oligofructose, inulin, inulin-type fructans), galactooligosaccharides, amino acids, alcohols, water-soluble cellulose derivatives (most preferably, methylcellulose, methyl ethyl cellulose, hydroxyethyl cellulose, ethyl hydroxyethyl cellulose, cationic hydroxyethyl cellulose, hydroxypropyl cellulose, hydroxyethyl methylcellulose, hydroxypropyl methylcellulose, and carboxymethyl cellulose), water-insoluble cellulose derivatives (most preferably, ethyl cellulose), unprocessed oatmeal, metamucil, all-bran, and any combinations thereof.

In some embodiments, the present invention provides pharmaceutical compositions that are formulated for administration to a subject or a patient, e.g., some embodiments provide pharmaceutical compositions formulated for administration to a human. Some embodiments provide pharmaceutical compositions for administration to a livestock animal, e.g., a chicken, cow, goat, pig, or sheep or a companion animal, e.g., dog, cat, etc. Related embodiments provide a pharmaceutical composition comprising live modified AIEC.

In some embodiments, the present invention provides pharmaceutical compositions formulated for various routes of administration, e.g., for providing the modified AIEC to the gastrointestinal tract. For example, in certain embodiments, the pharmaceutical composition is formulated for oral administration, and in some embodiments the pharmaceutical composition is formulated for rectal administration. In other embodiments, the pharmaceutical composition is a nutraceutical or a food.

T84 intestinal epithelial cells were infected with indicated bacteria at a MOI of 10. The number of adhered bacteria per cell (A) and the percentage of internalized bacteria compared with the number of initial bacteria (B). (C) Inhibitory effect of competitor strains was determined by inhibition halo assay on lawns of target strains. Red-filled boxes indicate halo formation while white-filled boxes indicate no halo formation in the presence of 0 to 2 log fold dilution of competitor strain. (D) LF82 was cultured alone or co-cultured with indicated bacteria at 1:1 for 3 hr, then the percentage of co-cultured LF82 compared with culture of LF82 alone was calculated. WT; NI1429Str, Δwzy; NI1429StrΔwzy, ΔcolY; NI1429StrΔcolY. Error bars represent SEM. *p<. 05, p<01, *p<001.

Figure 3:
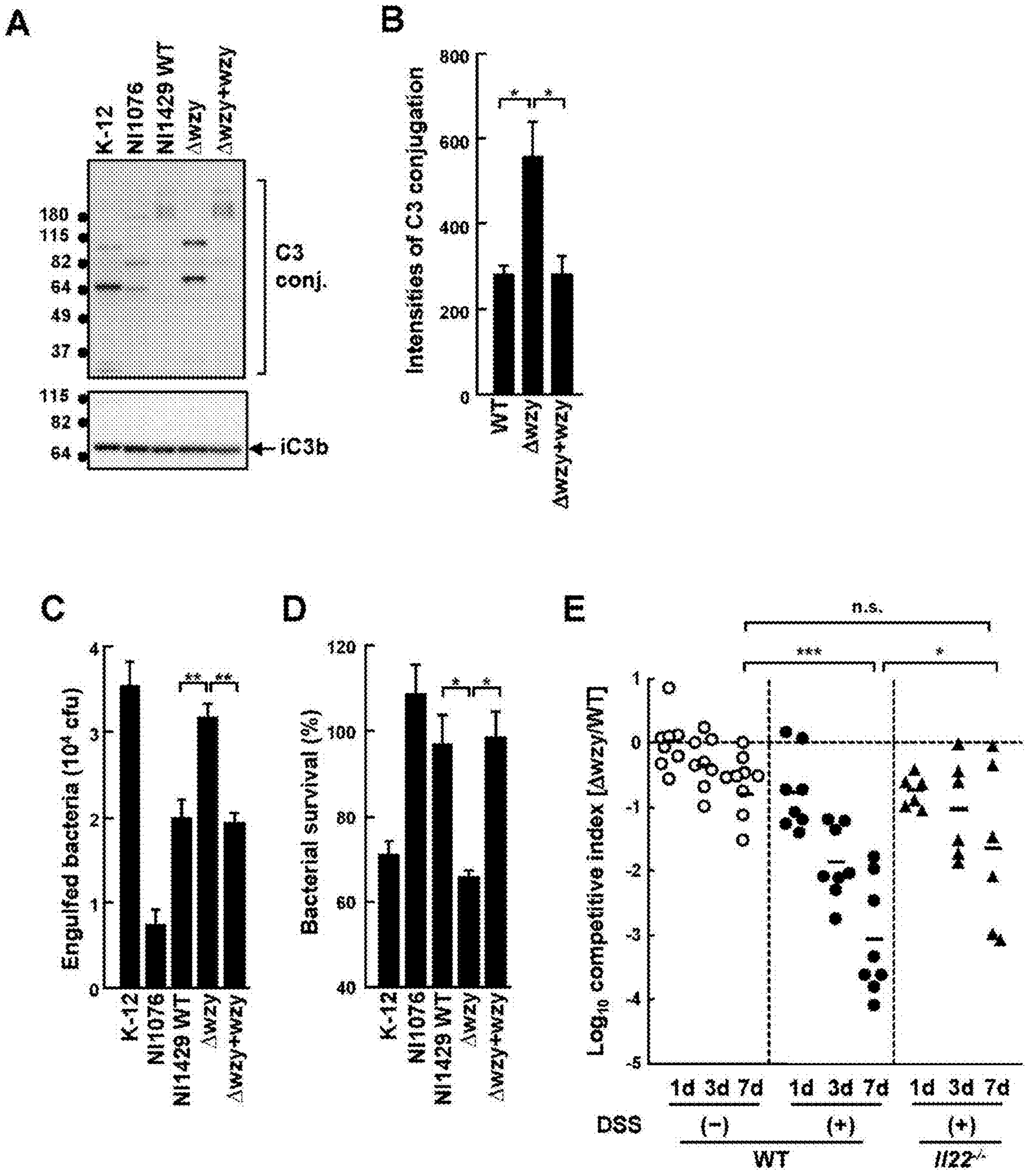

FIG. 3. Colitis-associated *E. coli* isolates exhibit complement resistance through O antigen structure.

(A and B) Indicated bacteria were incubated with fresh mouse serum for 30 min. (A) C3 deposition on bacteria (upper panel) and C3 processing (lower panel) were determined by immunoblotting. (B) Quantification of C3 deposition on indicated bacteria (n=4). (C) Bone marrow macrophages were incubated with the indicated bacterial strains in 5% fresh mouse sera. Internalized bacteria were counted after treatment with gentamicin (n=3). (D) Peritoneal neutrophils were incubated with the indicated strains in 2.5% fresh mouse serum for 2 hr. Surviving bacteria were counted by plating (n=3). Δwzy; NI1429Str Δwzy, Δwzy+wzy; NI1429StrΔwzy[pGEM®-T-wzy]. (E) WT and $Il22^{-/-}$ mice were inoculated with a mixture of equal numbers of NI1429Str (WT) and NI1429StrΔwzy::Cm (Δwzy) bacteria after treatment with streptomycin for 1 day, followed by administration of DSS or mock for 7 days and regular water for 1 day. The numbers of WT and the wzy mutant bacteria were determined after the indicated days of DSS treatment and used to measure the competitive index. Competitive index was calculated by logarithmic ratio of number of Δwzy against number of WT at the indicated time points (WT; n=8, $Il22^{-/-}$; n=6). Data represent pooled results from two independent experiments. Error bars represent SEM. *p<. 05, **p<. 01.

Figure 4:
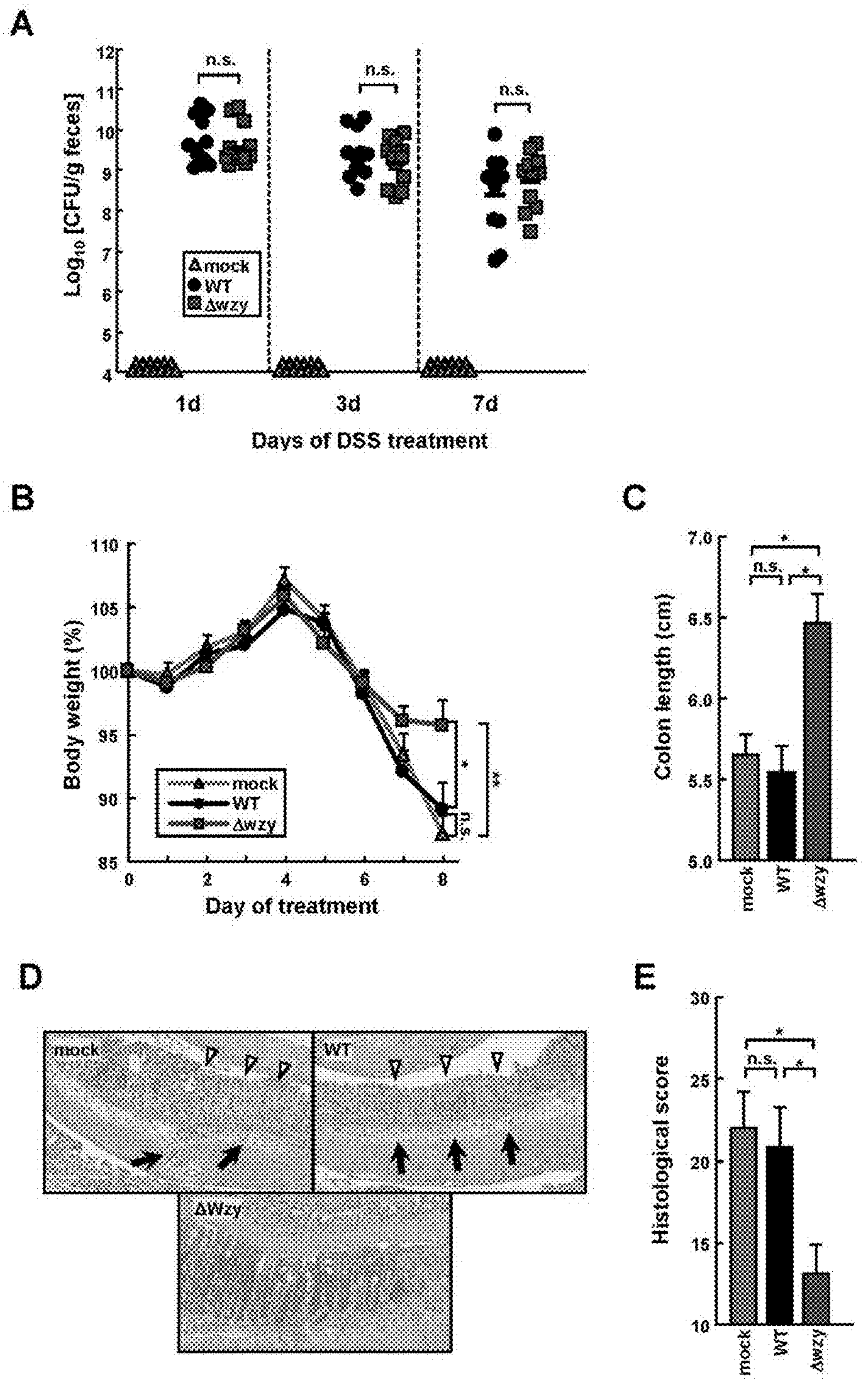

FIG. 4. The wzy AIEC mutant alleviates DSS-induced colitis.

WT mice were inoculated with $1\times10^8$ CFU of NI1429Str (WT), NI1429StrΔwzy::Cm (Δwzy) or mock after administration of streptomycin (2 mg/ml) in the drinking water for 1 day, followed by DSS treatment for 7 days and regular water for 1 day (n=13 per group). (A) The numbers of bacteria in feces were determined at the indicated time points. $10^4$ CFU/g represents the limit of detection using our plating method. (B) Body weight change was monitored over 8 days after treatment with DSS and 1 day of regular water. (C) Colon length. (D and E) Representative histology of HE-stained colonic sections (D) and histological scores (E) of colons from indicated mice after 7 days of DSS treatment and 1 day of regular water (n=8 per group). Open arrowheads indicate mucosal ulcer with total loss of the epithelium. Solid arrows indicate presence of submucosal and transmural inflammation and edema. Data represent pooled results from three independent experiments. Error bars represent SEM. *p<. 05, **p<. 01.

Figure 5:
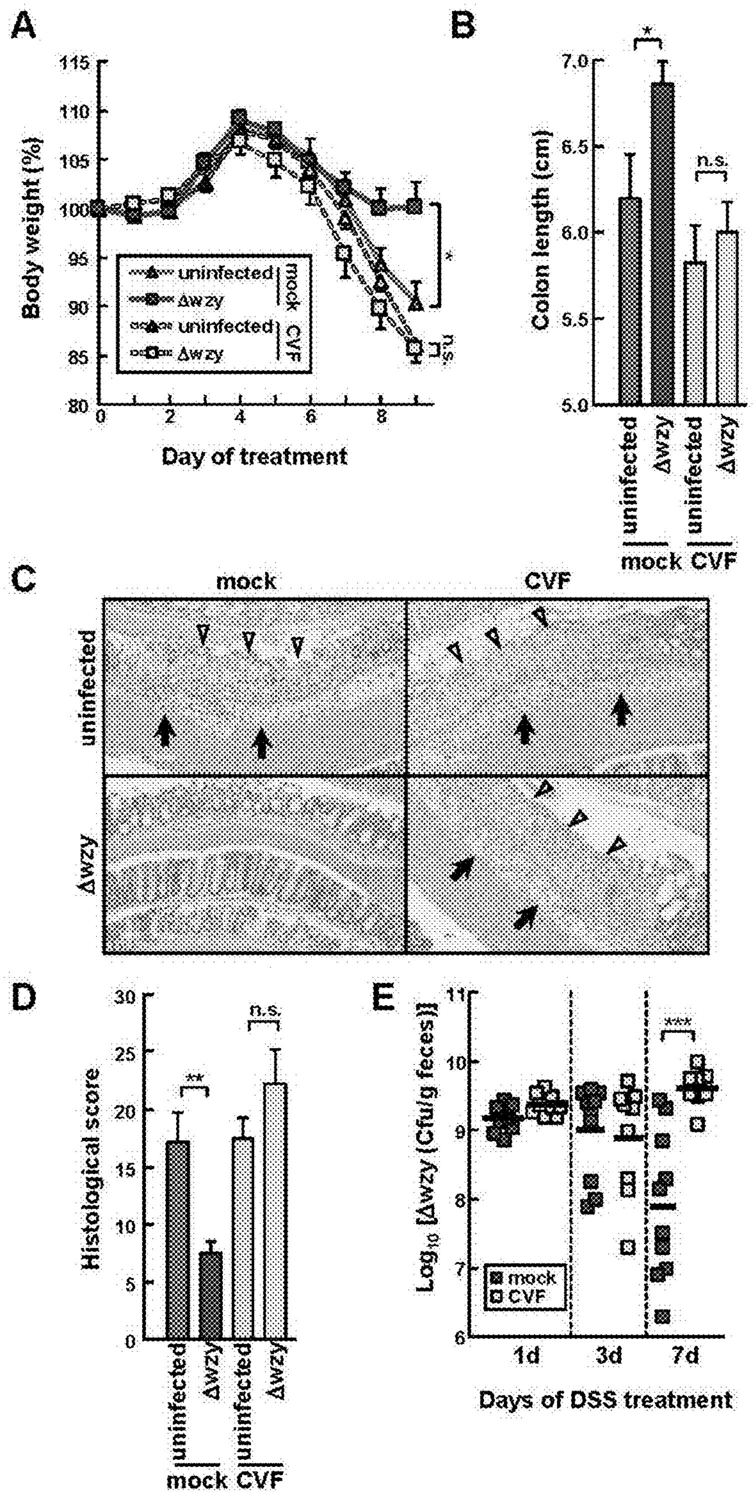

FIG. 5. Host protection by the wzy AIEC mutant depends on complement C3

WT mice colonized with NI1429StrΔwzy::Cm (Δwzy) were treated intraperitoneally with cobra venom factor (CVF, 25 μg/body) or mock 1 day before and on day 1, 4, 7 after DSS treatment. Mice were given DSS in the drinking water for 7 days followed by regular water for 2 days (n=10 per group). (A) Body weight change was monitored over 9 days after treatment with CVF or mock and DSS (B) Colon length. (C and D) Representative histology of HE-stained colonic sections (C) and histological scores (D) of colons from indicated mice after 7 days of DSS treatment. (E) The number of Δwzy bacteria in feces was determined after the indicated days of DSS treatment. Data represent pooled results from two independent experiments. Error bars represent SEM. *p<05, p<01, *p<001

Figure 1:
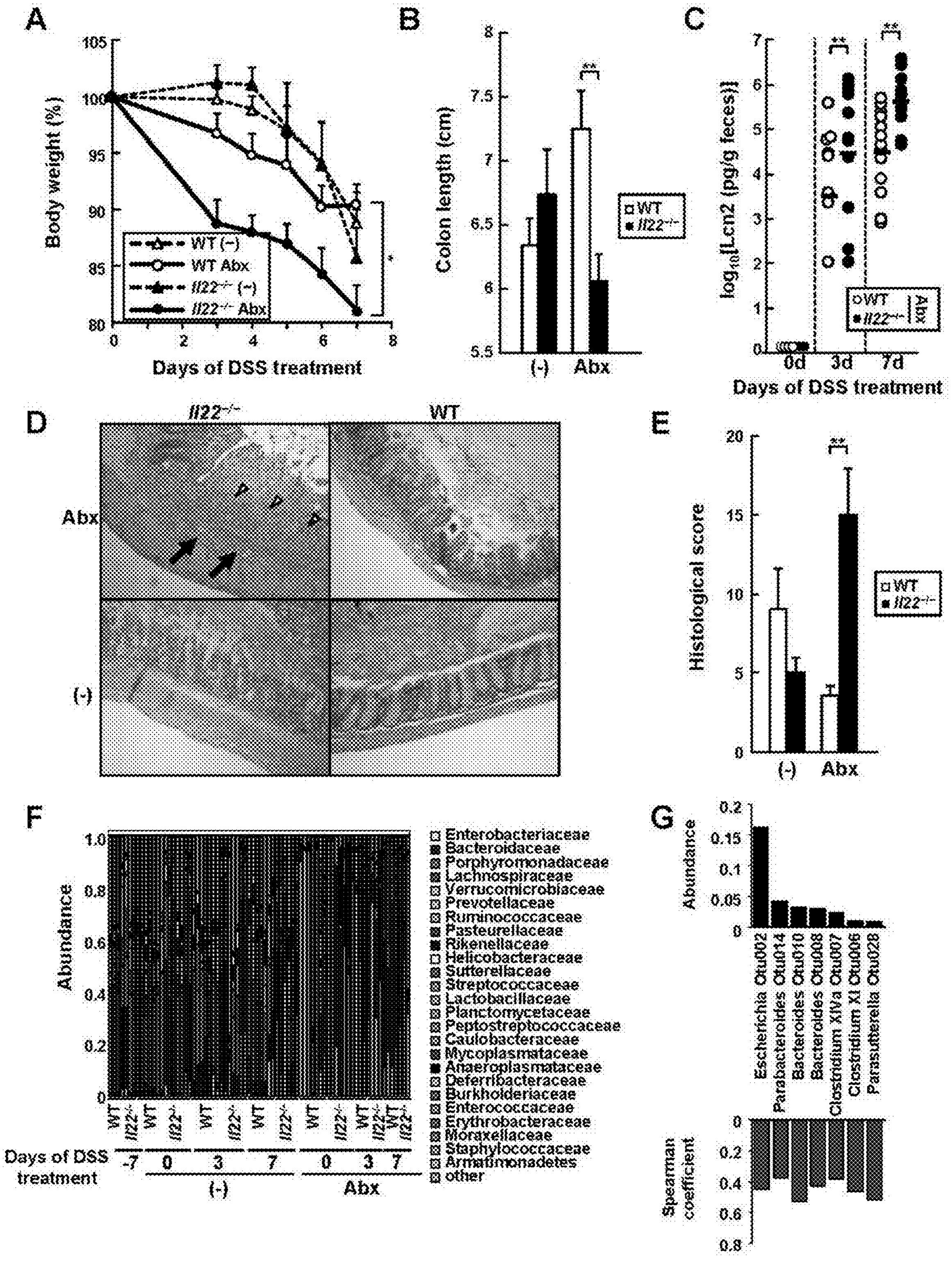
FIG. 1. Bacterial dysbiosis induced by antibiotic treatment regulates DSS-induced colitis in IL-22 deficient mice WT and $Il22^{-/-}$ mice were pretreated with the antibiotic cocktail (Abx) or mock (−) for six days after co-housing. Mice were given 2.5% DSS in the drinking water. Mice were monitored for body weight (A, n=9 to 22 per group), colon length after 7 days of DSS treatment and (B) fecal lipocalin-2 (Lcn2) levels (C) on the indicated days of DSS treatment. (D and E) representative histology of hematoxylin and eosin (HE)-stained colonic sections (D) and histological scores (E) of colons from indicated mice 7 days after DSS treatment (n=4-7 per group). Open arrowheads and solid arrows indicate mucosal ulcer with total loss of epithelium, and edema with submucosal inflammation, respectively. (F) Taxonomic microbiota composition at the family level in mice before antibiotic treatment (day-7), on day 6 after antibiotic treatment (day 0 of DSS treatment), and on day 3 and 7 after DSS treatment (n=3 to 7). (G) *Escherichia* is the most abundant bacteria that are associated with Lcn2 levels during DSS treatment. The bacteria that showed significant association (p<0.05) by Spearman's rank correlation analysis with OTU abundance and fecal lipocalin 2 levels in colitic intestine of DSS-treated mice. Error bars represent SEM. *p<. 05, **p<. 01.
Figure 6:
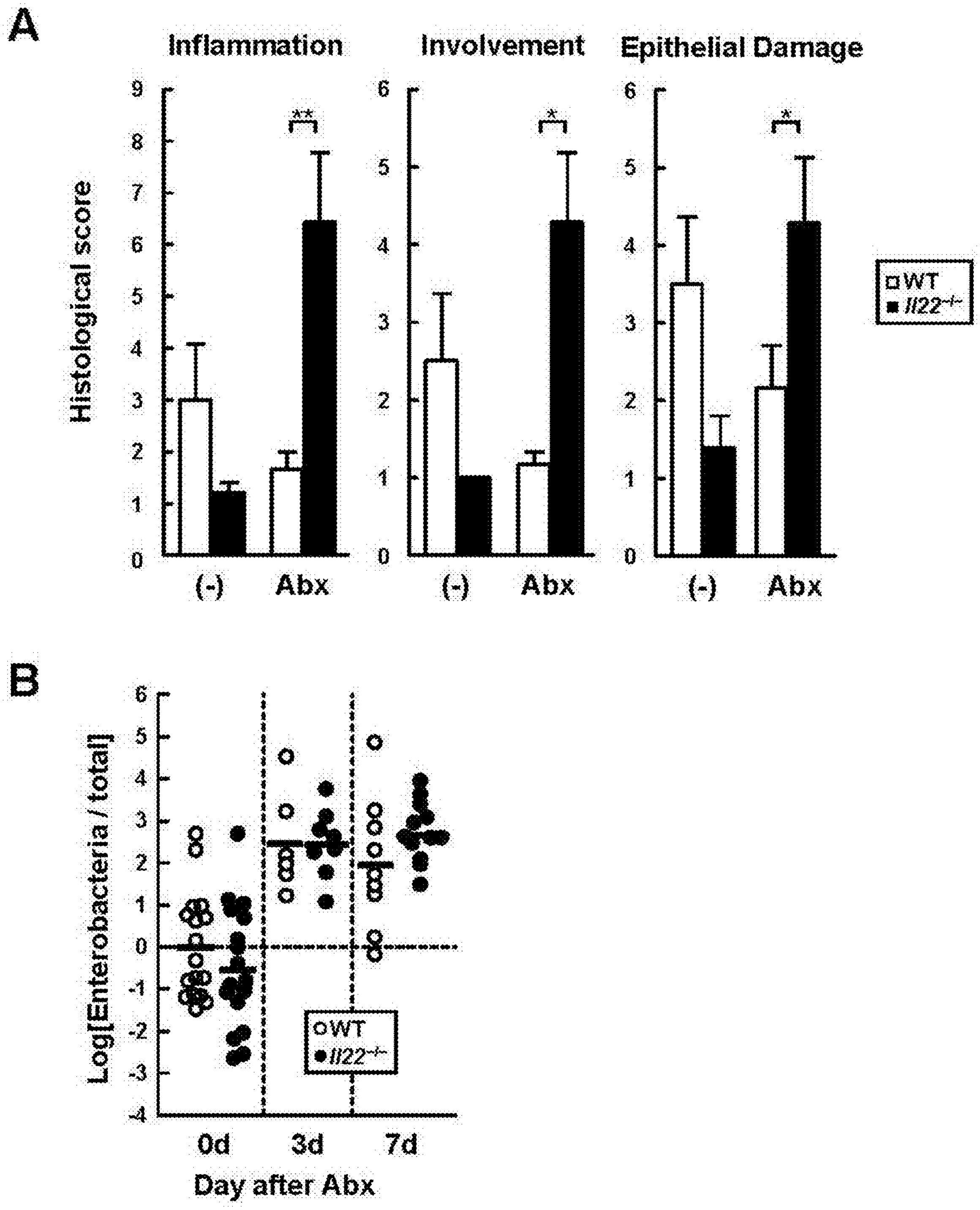

FIG. 6. Detailed histological scores and abundance of Enterobacteriaceae by qPCR shown in FIG. 1.

(A) Individual parameters of histological scores shown in FIG. 1E. (B) Abundance of Enterobacteriaceae quantified by qPCR shown in FIG. 1A. Values were normalized to the mean of day 0.

Figure 7:
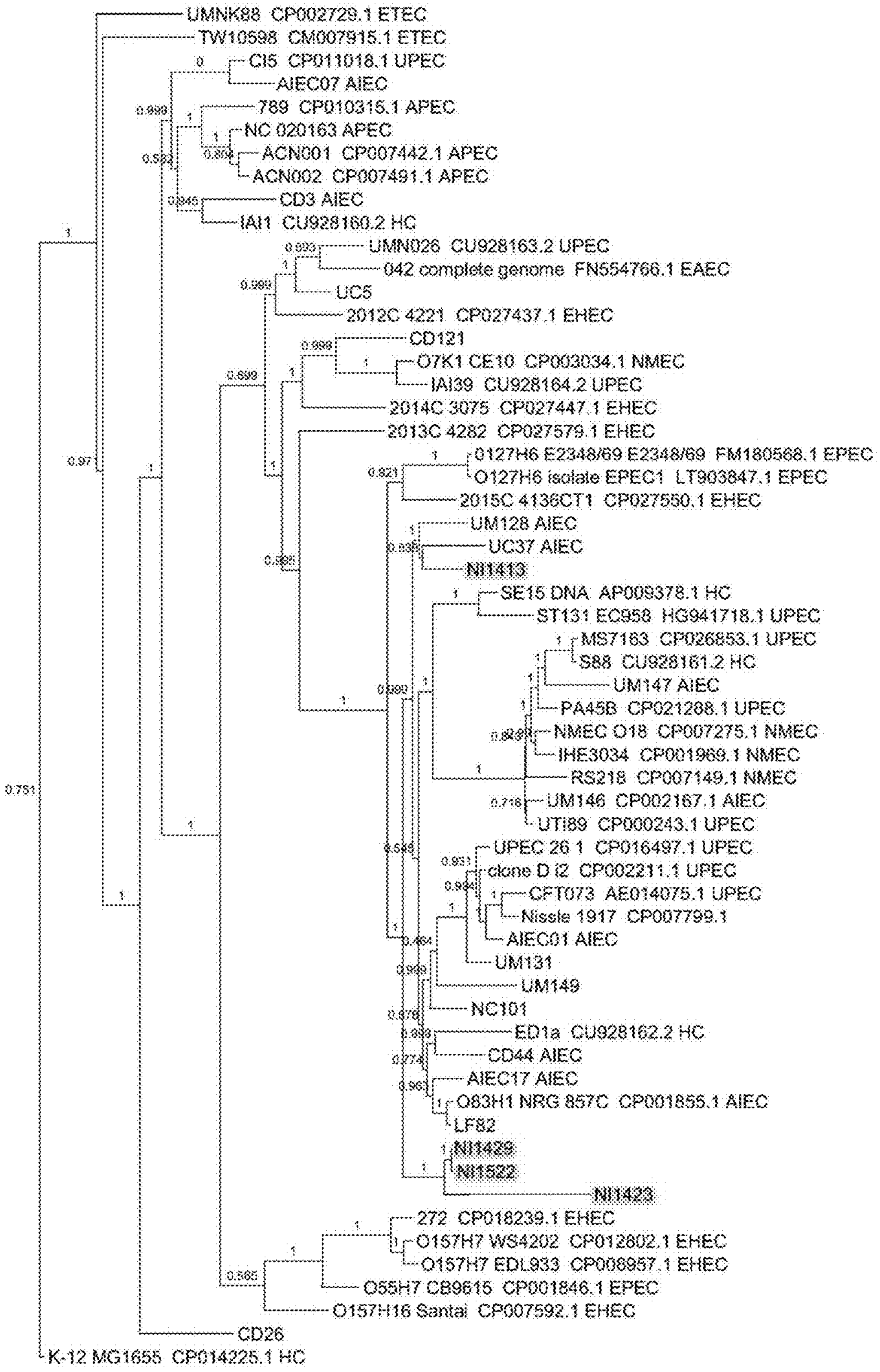
Figure 7:
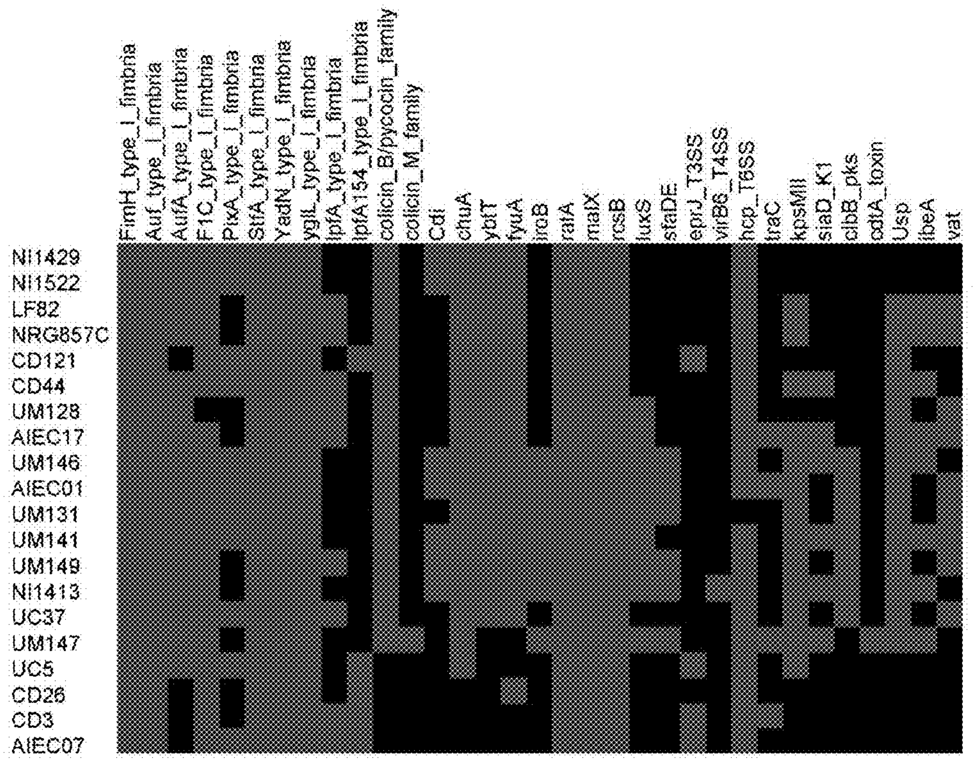
Figure 7:
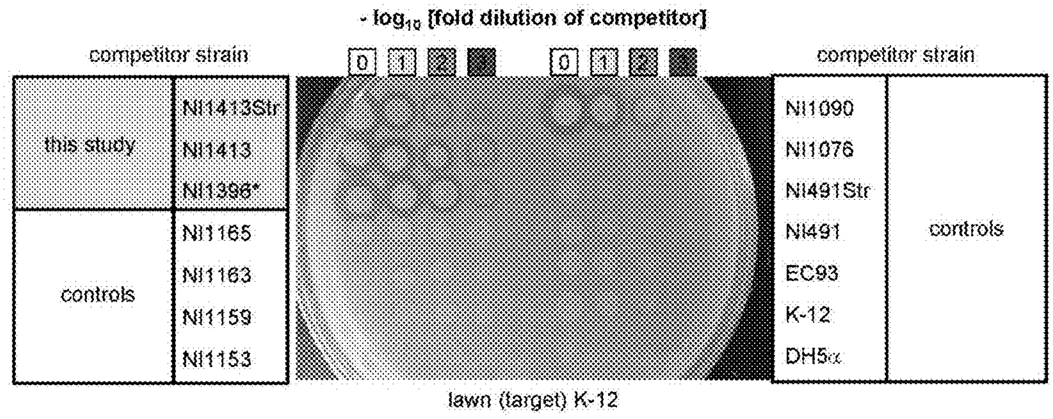

FIG. 7. Phylogenetic distances, virulence genes, and competition assay of *E. coli* strains.

(A) Phylogenetic tree of colitis-associated *E. coli* and representative non-AIEC strains. Phylogenetic distance was calculated as indicated in Methods. Colitis-associated *E. coli* isolates used in this study are highlighted in yellow. (B) AIEC-related putative virulence genes found in the genomes of *E. coli* isolates NI1413, NI1429, NI1522 and reference AIEC strains. Red denotes the presence while black indicates the absence of the gene. (C) Representative images of halo assay performed on the lawn of K-12 target cells. The tested competitors were NI1413 and its derivative NI1413Str, NI1396, another strain isolated from colitic Il22−/− mice, isolates from *C. difficile* infected Il22−/− mice (NI1165, NI1163, NI1159, NI1153, NI1090, [6]), NI491 isolated from feces of normal mice [6], and its derivative NI491Str, K-12 and its derivative DH5α. The details of the halo assay are described in Materials and Methods.

Figure 8:
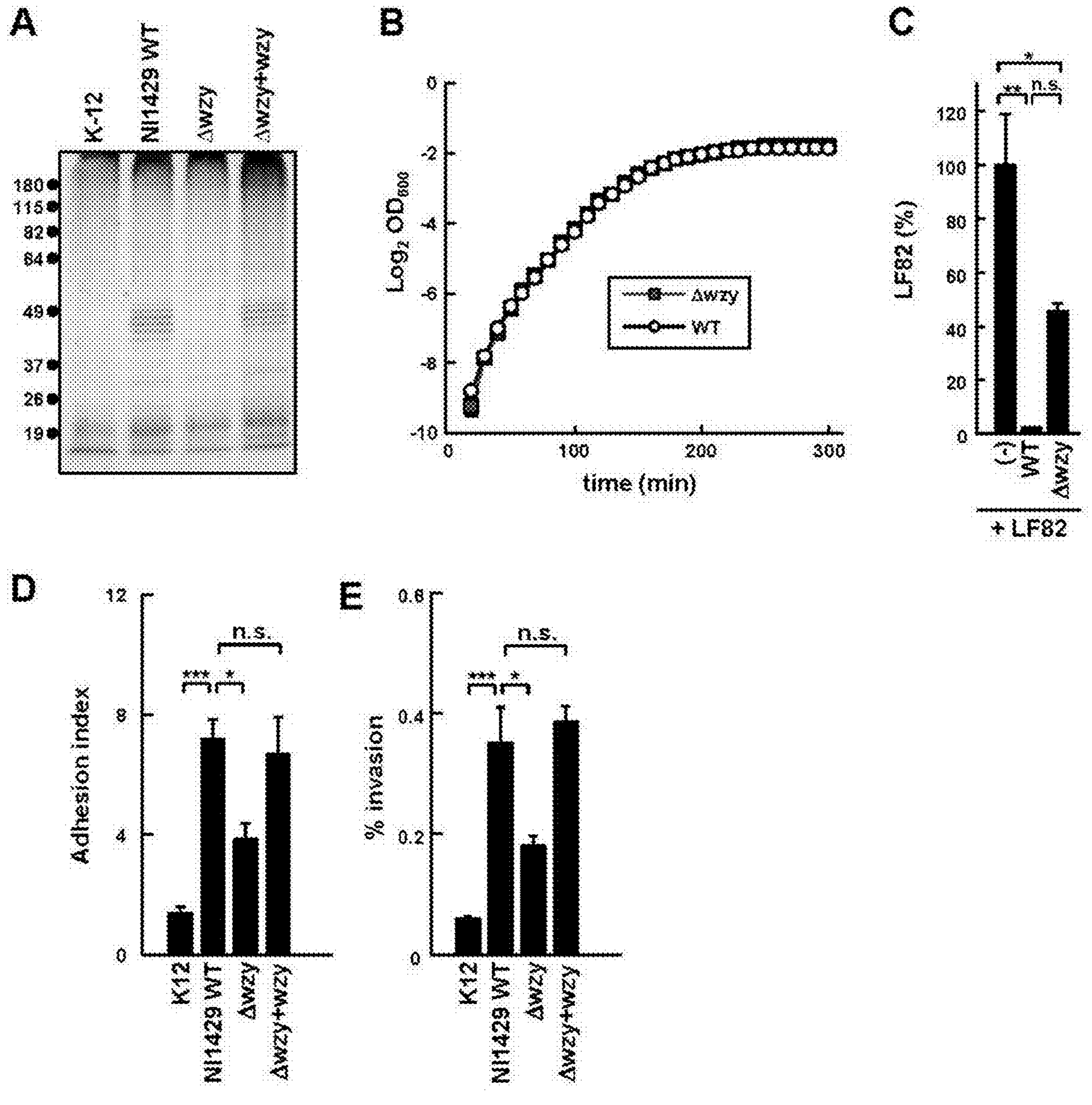

FIG. 8. LPS structure, growth rate, inhibitory effect on growth of LF82, and adhesion and invasion activity of WT and Δwzy *E. coli.* strains.

(A) Extracted LPS from indicated bacteria was visualized with silver staining. (B) Bacteria (optical density (OD), 0.01) was grown in L-broth, and OD was continuously monitored. K-12; K-12 substr. MG1655, Δwzy; NI1429StrΔwzy::Cm, Δwzy+wzy; NI1429StrΔwzy [pGEM®-T-wzy]. (C) LF82 was cultured alone or co-cultured with indicated bacteria at 1:1 for 3 hr, then the percentage of co-cultured LF82 bacteria compared with LF82 cultured alone was calculated. (D and E) T84 intestinal epithelial cells were infected with indicated bacteria at a MOI of 10. The number of adhered bacteria per cell (D) and the percentage of internalized bacteria compared with the number of initial bacteria (E) are shown. WT; NI1429Str, Δwzy; NI1429StrΔwzy, Δwzy+wzy;NI1429StrΔwzy [pGEM®-T-wzy]. Error bars represent SEM. *p<. 05, **p<. 01.

Figure 9:
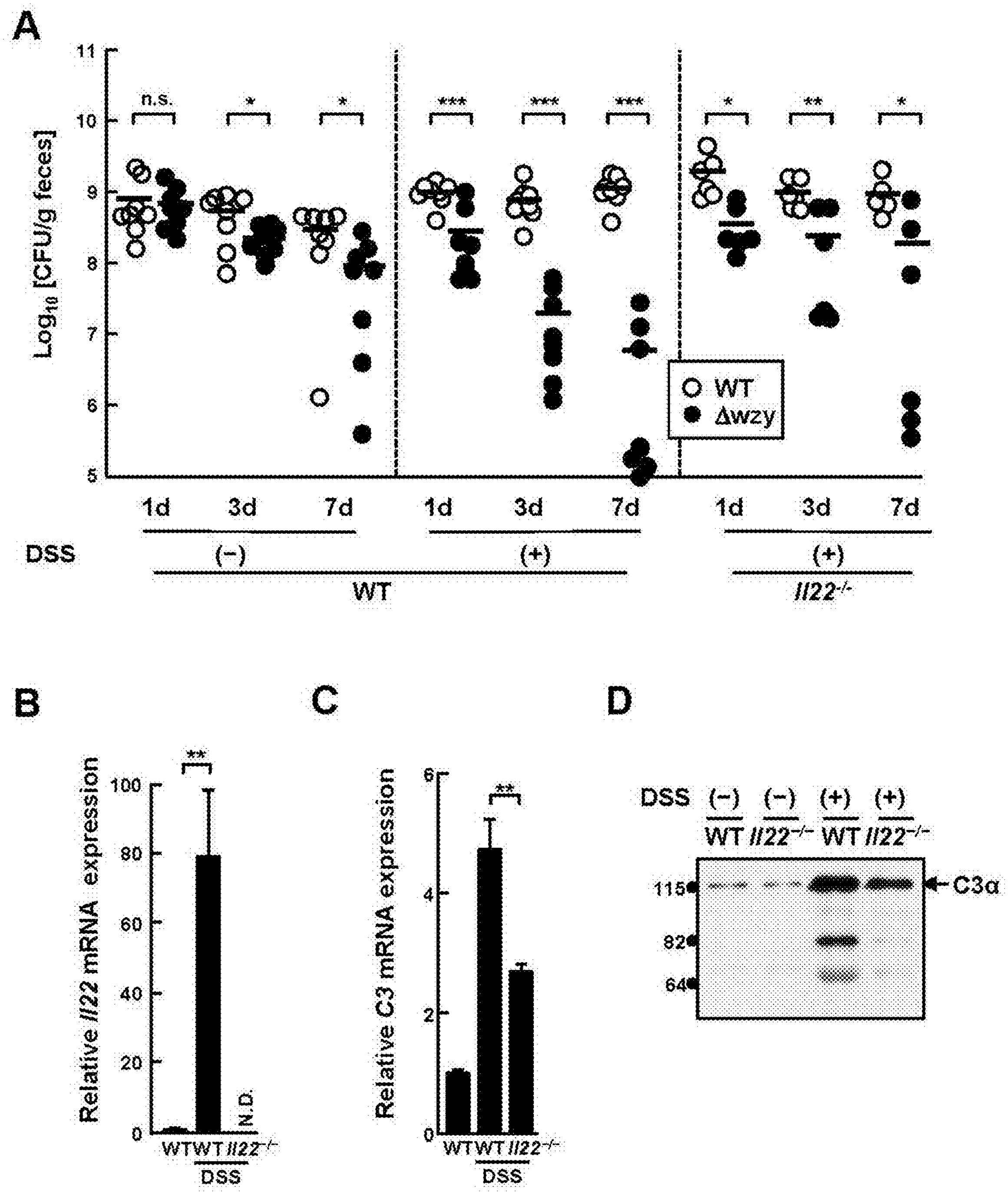

FIG. 9. IL-22-dependent augmentation of C3 deposition on colitis-associated *E. coli.*

(A) WT and Il22−/− mice were inoculated with a mixture of equal numbers of NI1429Str (WT) and NI1429StrΔwzy::Cm (Δwzy) bacteria after treatment with streptomycin for 1 day, followed by administration of DSS or mock for 7 days and regular water for 1 day. The numbers of WT and the wzy mutant bacteria were determined by plating at the indicated time points. The results from this experiment correspond to those shown in FIG. 3E. (B) Relative expression levels of Il22 mRNA in the colon of WT and Il22−/− mice treated with or without DSS. N. D., not detected. (C) mRNA expression levels of C3 in the liver of WT mice, DSS-treated WT mice, and DSS-treated Il22−/− mice. (n=5-6) (D) C3 levels in serum of WT mice, DSS-treated WT mice, and DSS-treated Il22−/− mice. WT; NI1429Str, Δwzy; NI1429StrΔwzy. Error bars represent SEM. *p<05, **p<01.

Figure 10:
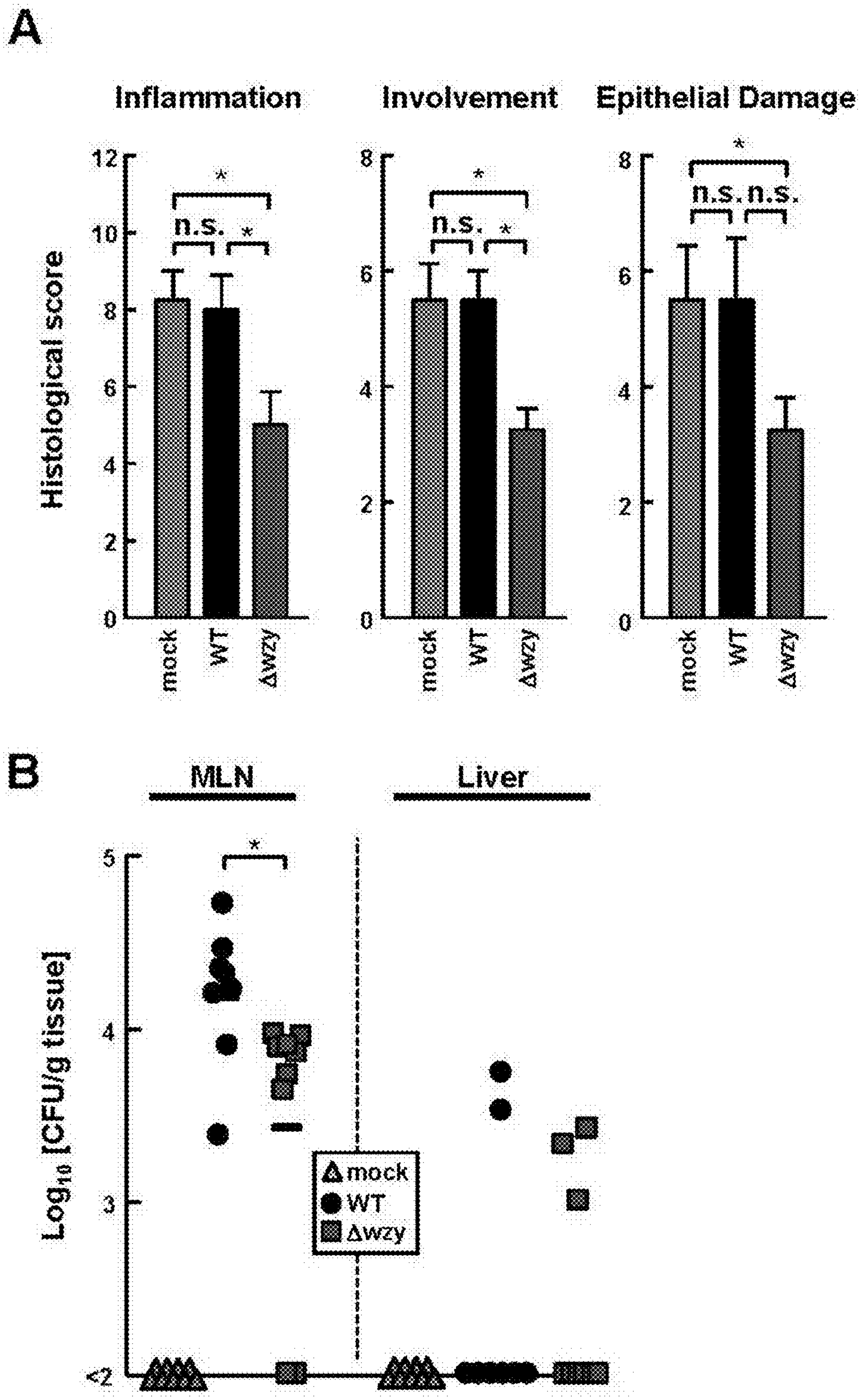

FIG. 10. Decreased bacterial loads of the wzy AIEC mutant in the mesenteric lymph nodes after DSS treatment (A) Individual parameters of histological scores shown in FIG. 4E. (B) The numbers of tested bacteria in mesenteric lymph node (MLN) and liver after 7 days of DSS treatment and 1 day of regular water. Error bars represent SEM. *p<0.05.

Figure 11:
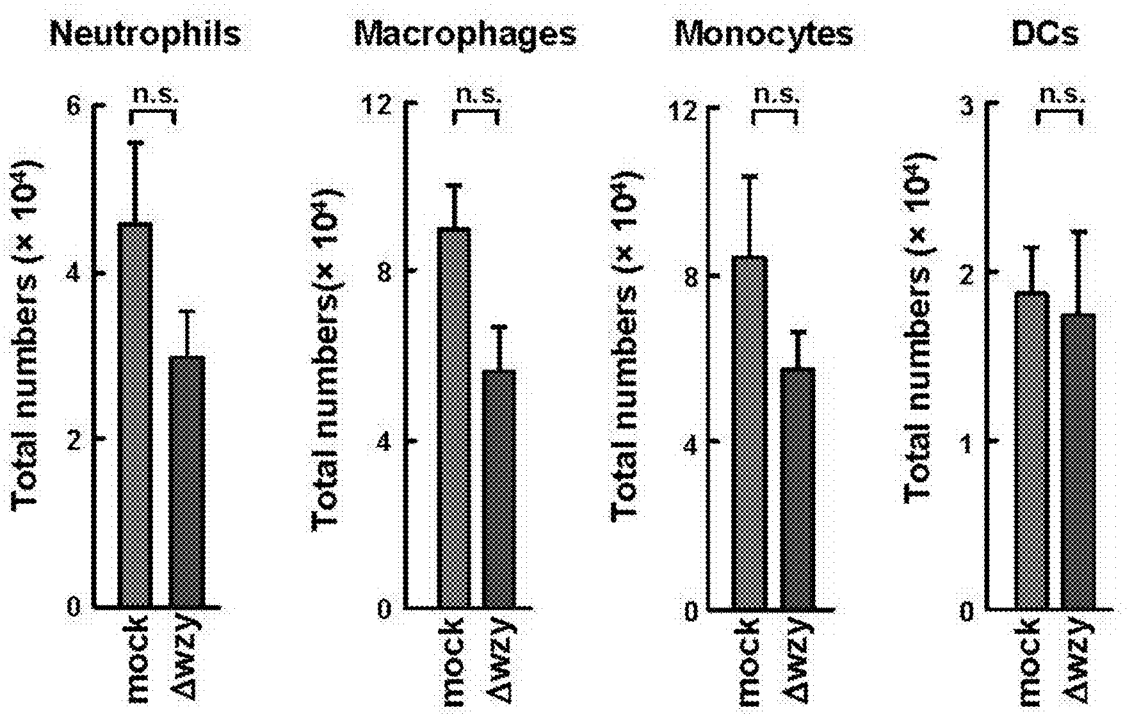

FIG. 11. Similar numbers of macrophages, neutrophils and dendritic cells in the intestinal tissue of WT- and Δwzy-colonized mice after 7 days of DSS treatment.

Absolute numbers of macrophages (CD45+ CD11b+ MHC II+Ly6C−), monocytes (CD45+ CD11b+ LY6C+ MHC II−), DCs (CD45+ CD11c+ MHC II+) and neutrophils (CD45+ CD11b+ Ly6G+) in the colon (n=4-5).

Figure 12:
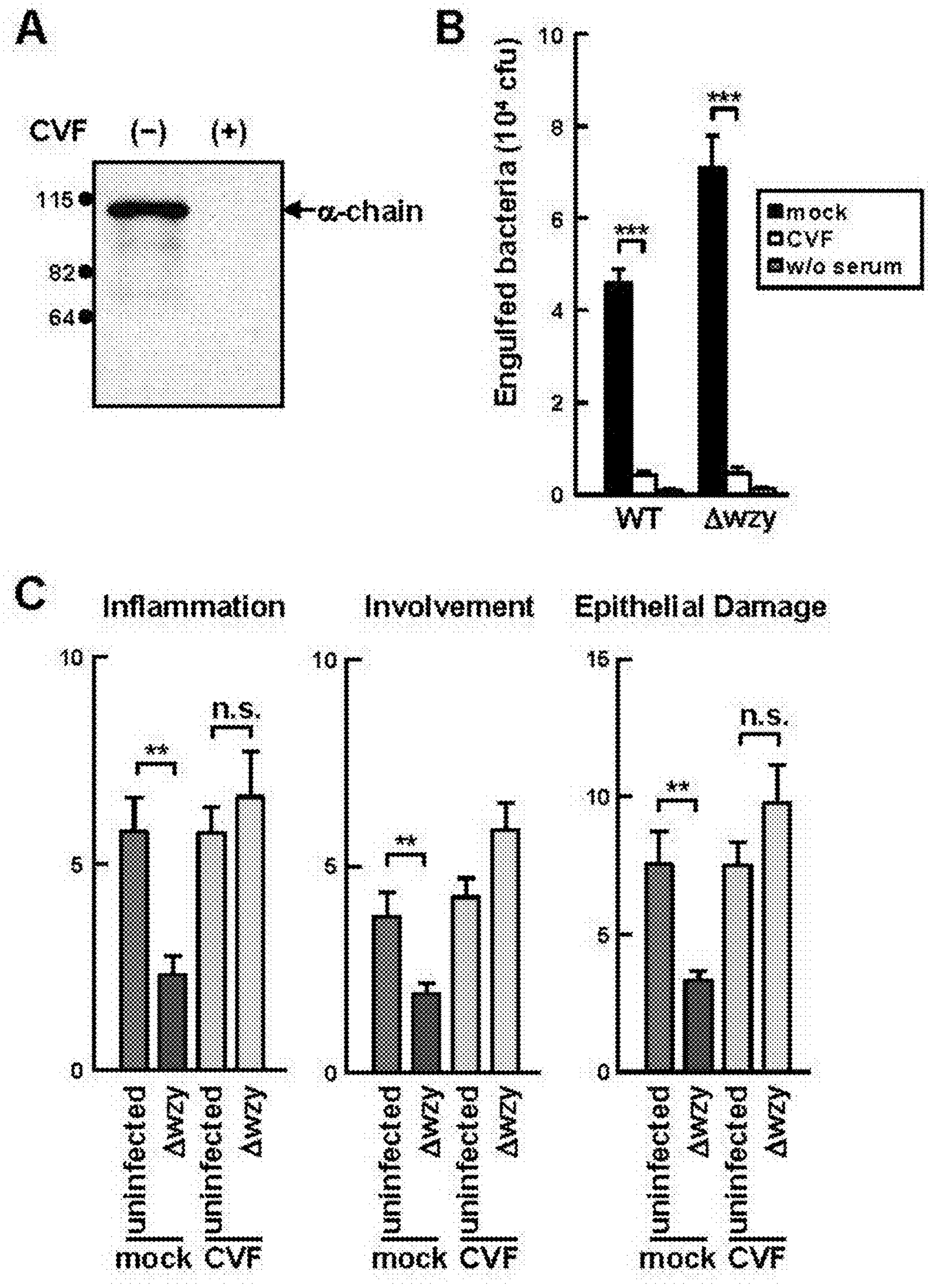

FIG. 12. C3 depletion and engulfment activity after treatment with CVF, and detailed histological scores shown in FIG. 5.

(A) Sera were collected from WT mice treated intraperitoneally with 25 μg/body of cobra venom factor or mock. Serum C3 was determined by immunoblotting. (B) Bone marrow macrophages were incubated with the indicated bacterial strains with or without 5% sera from WT mice treated with 25 μg/body of cobra venom factor or mock. Internalized bacteria were counted after treatment with gentamicin (n=3). (C) Individual parameters of histological scores shown in FIG. 5C. Data represent pooled results from two independent experiments. Error bars represent SEM. ***p<0.001.

Figure 13:
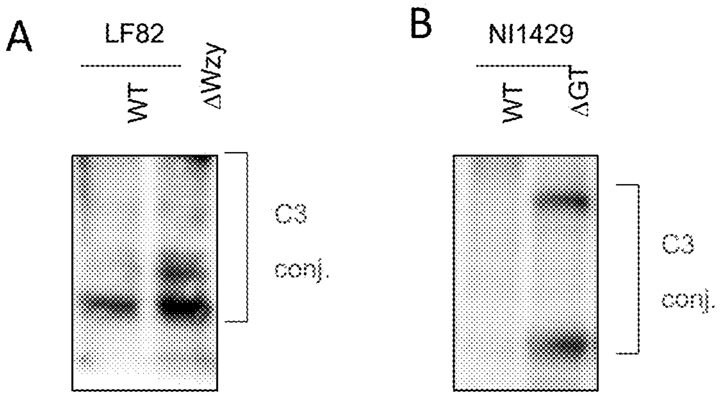

FIG. 13. C3 processing and deposition on wildtype and mutant bacterial strains.

(A) Shows generation of a wzy mutation in reference human *E. coli* strain LF82. The mutation is associated with increased complement deposition on the surface of bacteria. (B) Shows increased complement C3 conjugation and deposition on mouse *E. coli* strain N1429. $5\times10^8$ CFU of wild-type (WT) or mutant bacteria were incubated in mouse serum for 30 min and C3 subfragments deposited on bacteria were detected by immunoblotting with anti-C3 antibody. Abbreviations: C3 conj, complement C3 conjugated with bacteria; DWzy, LF82DWzy; DGT, NI1429DGT

DEFINITIONS

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "an AIEC" is a reference to one or more AIEC strains, unless the context clearly dictates otherwise.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "subject" broadly refers to any animal, including but not limited to, human and non-human animals (e.g., dogs, cats, cows, horses, sheep, poultry (e.g., chickens), fish, crustaceans, etc.). As used herein, the term "patient" typically refers to a subject that is being treated for a disease or condition.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), gastric, skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., a pharmaceutical composition comprising an AIEC and/or additional therapeutics) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintegrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

As used herein, the term "microbe" refers to cellular prokaryotic and eukaryotic species from the domains Archaea, Bacteria, and Eukarya, the latter including yeast and filamentous fungi, protozoa, algae, or higher Protista, and encompasses both individual organisms and populations comprising any number of the organisms. The terms "microbial cells" and "microbes" are used interchangeably with the term "microorganism".

The term "prokaryotes" refers to cells that contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The terms "bacteria" and "bacterium" and "archaea" and "archaeon" refer to prokaryotic organisms of the domain Bacteria and Archaea in the three-domain system (see Woese C R, et al., Proc Natl Acad Sci USA 1990, 87:4576-79).

The term "genus" is defined as a taxonomic group of related species according to the Taxonomic Outline of Bacteria and Archaea (Garrity et al. (2007) The Taxonomic Outline of Bacteria and Archaea. TOBA Release 7.7, March 2007. Michigan State University Board of Trustees).

The term "species" is defined as collection of closely related organisms with greater than 97% 16S ribosomal RNA sequence homology and greater than 70% genomic hybridization and sufficiently different from all other organisms so as to be recognized as a distinct unit (e.g., an operational taxonomic unit).

The term "strain" as used herein in reference to a microorganism describes an isolate of a microorganism considered to be of the same species but with a unique genome and, if nucleotide changes are non-synonymous, a unique proteome differing from other strains of the same organism. Strains may differ in their non-chromosomal genetic complement. Typically, strains are the result of isolation from a different host or at a different location and time, but multiple strains of the same organism may be isolated from the same host.

As used herein, the term "microbiota" or "microbiota" refers to an assemblage of microorganisms localized to a distinct environment. Microbiota may include, for example, populations of various bacteria, eukaryotes (e.g., fungi), and/or archaea that inhabit a particular environment. For example, "gut microbiota," "vaginal microbiota," and "oral microbiota" refer to an assemblage of one or more species of microorganisms that are localized to, or found in, the gut, vagina, or mouth, respectively.

"Normal microbiota" refers to a population of microorganisms that localize in a particular environment in a normal, non-pathological state (e.g., a sample of gut microbiota from a subject without intestinal inflammation). A "normal microbiota" has normal membership and normal relative abundance.

"Abnormal microbiota" refers to a population of various microorganisms that localize in a particular environment that differs from the normal microbiota in terms of identity (e.g., membership), absolute amount, or relative amount (e.g., relative abundance) of the various microbes.

"Pathologic microbiota" refers to a population of various microorganisms that localize in a particular environment in a pathological state and that differs from the normal microbiota in terms of identity (e.g., membership), absolute amount, or relative amount (e.g., relative abundance) of the various microbes.

As used herein, the term "commensal microbe" refers to a microorganism that is non-pathogenic to a host and is part of the normal microbiota of the host.

As used herein, the terms "microbial agent," "commensal microbial agent," and "probiotic" refer to compositions comprising a microbe or population of multiple different microbes for administration to a subject.

The terms "pathogen" and "pathogenic" in reference to a microorganism includes any such microorganism that is capable of causing or affecting a disease, disorder or condition of a host containing the microorganism.

As used herein, the terms "antibiotic" and "antibacterial agent" refer to a chemical agent which is active against bacteria. In common usage, an antibiotic is a substance or compound (also called chemotherapeutic agent) that kills or inhibits the growth of bacteria. Anti-bacterial antibiotics can be categorized based on their target specificity: "narrow-spectrum" antibiotics target particular types of bacteria, such as Gram-negative or Gram-positive bacteria, while broad-spectrum antibiotics affect a wide range of bacteria. Antibiotics which target the bacterial cell wall (e.g., penicillins, cephalosporins, cephems), or cell membrane (e.g., polymixins), or interfere with essential bacterial enzymes (e.g., quinolones, sulfonamides) usually are bactericidal in nature. Those which target protein synthesis such as the aminoglycosides, macrolides and tetracyclines are usually bacteriostatic. Three newer classes of antibiotics include: cyclic lipopeptides (e.g., daptomycin), glycylcyclines (e.g., tigecycline), and oxazolidinones (e.g., linezolid). Tigecycline is a broad-spectrum antibiotic, while the two others are useful for Gram-positive infections.

As used herein, the term "probiotic" refers to a microorganism that is a viable, non-pathogenic organism that confers health benefits to a host by improving microbial balance of indigenous flora. For example, an adherent, invasive *E. coli* (AIEC) bacteria is not a "probiotic" bacteria.

The term "mutation" as used herein indicates any modification of a nucleic acid that results in an altered nucleic acid, e.g., that produces an amino acid "substitution" in a polypeptide (e.g., thus producing a "mutant" polypeptide or "mutant" nucleic acid). Mutations include, for example, point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, an insertion, or a deletion of part or all of a gene. In addition, in some embodiments of the modified microorganism, a portion of the microorganism genome has been replaced with a heterologous polynucleotide. In some embodiments, the mutations are naturally-occurring. In other embodiments, the mutations are the results of artificial mutation pressure. In still other embodiments, the mutations in the microorganism genome are the result of genetic engineering.

The term "biosynthetic pathway", also referred to as "metabolic pathway", refers to a set of anabolic or catabolic biochemical reactions for converting one chemical species into another. Gene products belong to the same "metabolic pathway" if they, in parallel or in series, act on the same substrate, produce the same product, or act on or produce a metabolic intermediate (e.g., a metabolite) between the same substrate and metabolite end product.

A "facultative anaerobic organism" or a "facultative anaerobic microorganism" is defined as an organism that can grow in either the presence or in the absence of oxygen.

A "strictly anaerobic organism" or a "strictly anaerobic microorganism" is defined as an organism that cannot grow in the presence of oxygen and which does not survive exposure to any concentration of oxygen.

An "anaerobic organism" or an "anaerobic microorganism" is defined as an organism that cannot grow in the presence of oxygen.

"Aerobic conditions" are defined as conditions under which the oxygen concentration in the fermentation medium is sufficiently high for an aerobic or facultative anaerobic microorganism to use as a terminal electron acceptor.

In contrast, "anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of the fermentation until oxygen is unavailable to the microorganism as a terminal electron acceptor. "Anaerobic conditions" are further defined as conditions under which no or small amounts of oxygen are added to the medium at rates of <3 mmol/L/h, preferably <2.5 mmol/L/h, more preferably <2 mmol/L/h and most preferably <1.5 mmol/L/h. "Anaerobic conditions" means in particular completely oxygen-free (e.g., 0 mmol/L/h oxygen) or with small amounts of oxygen added to the medium at rates of, e.g., <0.5 to <1 mmol/L/h.

As used herein, the term "taxonomic unit" is a group of organisms that are considered similar enough to be treated as a separate unit. A taxonomic unit may comprise, e.g., a class, family, genus, species, or population within a species (e.g., strain), but is not limited as such.

As used herein, the terms "operation taxonomic unit," "OTU," and "taxon" are used interchangeably to refer to a group of microorganisms considered similar enough to be treated as a separate unit. In one embodiment, an OTU is a group tentatively assumed to be a valid taxon for purposes of phylogenetic analysis. In another embodiment, an OTU is any of the extant taxonomic units under study. In yet another embodiment, an OTU is given a name and a rank. For example, an OTU can represent a domain, a sub-domain, a kingdom, a sub-kingdom, a phylum, a sub-phylum, a class, a sub-class, an order, a sub-order, a family, a subfamily, a genus, a subgenus, a species, a subspecies, a strain, etc. In some embodiments, OTUs can represent one or more organisms from the domains Bacteria, Archaea, or Eukarya at any level of a hierarchal order. In some embodiments, an OTU represents a prokaryotic or fungal order. In some embodiments, an OTU is defined based on extent of homology between biomolecular (e.g., nucleic acid, polypeptide) sequences (e.g., percent identity). For example, in certain cases, the OTU may include a group of microorganisms treated as a unit based on, e.g., a sequence identity of ≥95%, ≥90%, ≥80%, or ≥70% among at least a portion of a differentiating biomarker, e.g., a biomolecule such as the 16S rRNA gene.

As used herein, a biomolecule (e.g., a nucleic acid or polypeptide) has "homology" or is "homologous" to a second biomolecule if the biomolecule sequence has a similar sequence to the second biomolecule sequence. The terms "identity," "percent sequence identity" or "identical" in the context of nucleic acid or polypeptide sequences refer to the residues (nucleotide bases or amino acids) in the two sequences that are the same when aligned for maximum correspondence. There are a number of different algorithms known in the art that can be used to measure sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990). The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, or at least about 90%, or at least about 95%, 96%, 97%, 98% 99%, 99.5% or 100% of the nucleotide bases, as measured by any well-known algorithm of sequence identity, such as FASTA, BLAST or Gap, as discussed above.

As used herein, a "colony-forming unit" ("CFU") is used as a measure of viable microorganisms in a sample. A CFU is an individual viable cell capable of forming on a solid medium a visible colony whose individual cells are derived by cell division from one parental cell.

As used herein, the term "relative abundance" relates to the abundance of microorganisms of a particular taxonomic unit or OTU in a test biological sample compared to the abundance of microorganisms of the corresponding taxonomic unit or OTU in one or more non-diseased control samples. The "relative abundance" may be reflected in e.g., the number of isolated species corresponding to a taxonomic unit or OTU or the degree to which a biomarker specific for the taxonomic unit or OTU is present or expressed in a given sample. The relative abundance of a particular taxonomic unit or OTU in a sample can be determined using culture-based methods or non-culture-based methods well known in the art. Non-culture based methods include sequence analysis of amplified polynucleotides specific for a taxonomic unit or OTU or a comparison of proteomics-based profiles in a sample reflecting the number and degree of polypeptide-based, lipid-based, polyssacharide-based or carbohydrate-based biomarkers characteristic of one or more taxonomic units or OTUs present in the samples. Relative abundance or abundance of a taxon or OTU can be calculated with reference to all taxa/OTUs detected, or with reference to some set of invariant taxa/OTUs.

Methods for profiling the relative abundances of microbial taxa in biological samples, including biological samples of gut microbiota, are well known in the art. Suitable methods may be sequencing-based or array-based. The microbial component of a gut microbiota sample is characterized by sequencing a nucleic acid suitable for taxonomic classification and assigning the sequencing reads to operational taxonomic units (OTUs) with a defined (e.g., >97%) nucleotide sequence identity to a database of annotated and representative sequences. An example of such a database is Greengenes version of May 2013, however any suitable database may be used. After OTUs are defined, a representative sequence from each OTU can be selected and compared to a reference set. If a match is identified in the reference set, that OTU can be given an identity. Relative abundance of a bacterial taxon may be defined by the number of sequencing reads that can be unambiguously assigned to each taxon after adjusting for genome uniqueness.

In some embodiments, a suitable nucleic acid for taxonomic classification is universally distributed among the gut microbial population being queried allowing for the analysis of phylogenetic relationships among distant taxa, and has both a conserved region and at least one region subject to variation. The presence of at least one variable region allows sufficient diversification to provide a tool for classification, while the presence of conserved regions enables the design of suitable primers for amplification (if needed) and/or probes for hybridization for various taxa at different taxonomic levels ranging from individual strains to whole phyla. While any suitable nucleic acid known in the art may be used, one skilled in the art will appreciate that selection of a nucleic acid or region of a nucleic acid to amplify may differ by environment. In some embodiments, a nucleic acid queried is a small subunit ribosomal RNA gene. For bacterial and archaeal populations, at least the V1, V2, V3, V4, V5, V6, V7, V8, and/or V9 regions of the 16S rRNA gene are suitable, though other suitable regions are known in the art. Guidance for selecting a suitable 16S rRNA region to amplify can be found throughout the art, including Guo et al. PLOS One 8(10) e76185, 2013; Soergel D A W et al. ISME Journal 6:1440, 2012; and Hamady M et al. Genome Res. 19:1 141, 2009, each hereby incorporated by reference in its entirety.

As used herein, the terms "detect", "detecting" or "detection" may describe either the general act of discovering or discerning or the specific observation of a detectably labeled composition.

The term "derivative" of a compound, as used herein, refers to a chemically modified compound wherein the chemical modification takes place either at a functional group of the compound or backbone.

The term "diagnosed," as used herein, refers to the recognition of a disease by its signs and symptoms (e.g., resistance to conventional therapies), or genetic analysis, pathological analysis, histological analysis, and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "toxic" refers to any detrimental or harmful effects on a cell or tissue as compared to the same cell or tissue prior to the administration of the toxicant.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include feces, urine, saliva, blood products, such as plasma, serum and the like. Environmental samples include environmental material such as surface matter, soil, water, and industrial samples. Such examples are not however to be construed as limiting the sample types applicable to the present invention.

As used herein, the term "modulate" refers to the activity of a compound (e.g., a compound described herein) to affect (e.g., to promote or retard) an aspect of cellular function, including, but not limited to, bacterial growth and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., bacterial inflammation). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that target virulence genes.

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

DETAILED DESCRIPTION

Provided herein are compositions and methods for the management of intestinal inflammation. In particular, compositions comprising modified adherent-invasive *E. coli* (AIEC) are administered to human and/or animal subjects to treat, prevent or decrease susceptibility to intestinal inflammation.

The surface of bacterial symbionts and pathogens is important for the interaction of these microorganisms with their hosts. On the cell surface, microbes express various conserved molecules, structures and antigens that can be recognized by the host immune system for microbe killing and eradication [1]. Conversely, many microbes can evade host recognition through the production of cell surface proteins and polysaccharides including the capsule (K-antigen) and lipopolysaccharide side chains (O-antigen) structures in Enterobacteriaceae [2,3]. These bacterial polysaccharides confer resistance to the host immune system by inhibiting the binding of antibodies to microbial surface antigens and impairing complement-mediated phagocytosis [4,5]. Thus, structural variation in surface polysaccharides produced by bacteria can affect the survival of microorganisms that invade host tissues as well as the susceptibility of the host to bacteremia and sepsis [6]. Extraintestinal pathogenic *Escherichia coli* (ExPEC) strains produce specific K or O serotypes and are often resistant to host systemic immunity [7, 8], while intestinal pathogenic *E. coli* (InPEC) strains can cause or promote colitis, diarrhea and inflammatory bowel disease (IBD) through their ability to interact with intestinal cells [9]. The host/bacterial interactions are primarily mediated by bacterial adhesive molecules and toxins, but the role of surface polysaccharides in the regulation of intestinal inflammation remains unknown.

Adherent-invasive *E. coli* (AIEC) is a group of InPEC that is associated with IBD including Crohn's disease (CD) and ulcerative colitis (UC) [10, 11]. AIEC expresses surface adhesins including type I fimbriae that are important for its ability to interact with host cells and for biofilm formation [12]. Structural variation of FimH in type I fimbria is associated with higher ability of AIEC to adhere to and invade host cells [13]. Furthermore, the invasiveness properties of AIEC have been suggested to be important for evading recognition and elimination by the host immune system [14, 15]. These observations indicate that the resistance of AIEC to host recognition and elimination impacts bacterial survival and the ability of AIEC to promote intestinal inflammation.

Multiple lines of evidence suggest that IBD is caused by genetic and environmental factors that alter intestinal homeostasis in genetically susceptible individuals [16]. Many IBD-associated loci are known to regulate the recognition and killing of bacteria as well as the function of immune cells [17]. For example, IL23R and TNFSF15 that are critical for the activation of innate lymphoid cells 3

(ILC3) and Th17 cells, cell populations that are important for the maintenance of the intestinal barrier and tissue repair, are associated with IBD susceptibility [18, 19]. ILC3 and Th17 cells produce IL-22, a cytokine that mediates protective immune responses in infectious and chemically-induced colitis [20]. Upon enteric bacterial infection, IL-22 is produced locally in the intestine, but can also reach the liver where it acts on hepatocytes to induce the secretion of acute phase proteins including complement protein C3 [6, 21]. In patients with IBD and animal models of colitis, there is an alteration in the composition and structure of the gut microbiota which includes a bloom of AIEC [22, 23]. Furthermore, colonization by certain AIEC strains can promote the induction of colitis in IL10-deficient mice [24]. In experiments conducted in the development of the present invention, Il22-mice were used to determine the role of surface lipopolysaccharide in the regulation of AIEC colonization and AIEC-associated colitis.

I. Compositions and Kits

Provided herein are methods, kits, and compositions for administering modified AIEC bacteria to a subject to promote healthy microbiota and thereby prevent and/or decrease susceptibility to intestinal inflammation, colitis and IBD. Accordingly, in some embodiments, the present technology provides compositions and kits, e.g., for administration to a subject. In some embodiments, compositions comprise one or more modified AIEC strains. The present invention is not limited to a particular one or more modified AIEC strain. Examples include, but are not limited to, those described herein.

In some embodiments, compositions comprise one or more additional components (e.g., including but not limited to, one or more additional additive(s) selected from the group consisting of an energy substrate, a mineral, a vitamin, or combinations thereof).

In some embodiments, bacteria are live cells, freeze-dried cells, etc. Freeze-dried bacteria can be stored for several years with maintained viability. In certain applications, freeze-dried bacteria are sensitive to humidity. One way of protecting the bacterial cells is to store them in oil. The freeze-dried bacterial cells can be mixed directly with a suitable oil, or alternately the bacterial cell solution can be mixed with an oil and freeze dried together, leaving the bacterial cells completely immersed in oil. Suitable oils may be edible oils such as olive oil, rapeseed oil which is prepared conventionally or cold-pressed, sunflower oil, soy oil, maize oil, cotton-seed oil, peanut oil, sesame oil, cereal germ oil such as wheat germ oil, grape kernel oil, palm oil and palm kernel oil, linseed oil. The viability of freeze-dried bacteria in oil is maintained for at least nine months. Optionally live cells can be added to one of the above oils and stored.

In some embodiments, compositions are added to nutraceuticals, food products, or foods. In some embodiments, to give the composition or nutraceutical a pleasant taste, flavoring substances such as for example mints, fruit juices, licorice, *Stevia rebaudiana*, steviosides or other calorie free sweeteners, rebaudioside A, essential oils like *eucalyptus* oil, or menthol can optionally be included in compositions of embodiments of the present invention.

In some composition embodiments, compositions are formulated in pharmaceutical compositions. The modified AIEC bacteria of embodiments of the invention may be administered alone or in combination with pharmaceutically acceptable carriers or diluents, and such administration may be carried out in single or multiple doses as described herein.

Compositions may, for example, be in the form of tablets, resolvable tablets, capsules, bolus, drench, pills sachets, vials, hard or soft capsules, aqueous or oily suspensions, aqueous or oily solutions, emulsions, powders, granules, syrups, elixirs, lozenges, reconstitutable powders, liquid preparations, creams, troches, hard candies, sprays, chewing-gums, creams, salves, jellies, gels, pastes, toothpastes, rinses, dental floss and tooth-picks, liquid aerosols, dry powder formulations, HFA aerosols or organic or inorganic acid addition salts.

The pharmaceutical compositions of embodiments of the invention may be in a form suitable for, e.g., rectal, oral, topical, buccal administration. Depending upon the disorder and patient to be treated and the route of administration, the compositions may be administered at varying doses.

In some embodiments, modified AIEC strains are formulated in pharmaceutical compositions for rectal administration. Such formulations include enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In some embodiments, modified AIEC strains are formulated in pharmaceutical compositions for oral administration. Oral dosage forms include push fit capsules made of gelatin, as well as soft, sealed capsules made of gelatin and a plasticizer, such as glycerol or sorbitol. In specific embodiments, push fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In some embodiments, the bacterial formulation comprises at least $1\times10^4$ CFU (e.g., $1\times10^4$ CFU, $2\times10^4$ CFU, $5\times10^4$ CFU, $1\times10^5$ CFU, $2\times10^5$ CFU, $5\times10^5$ CFU, $1\times10^6$ CFU, $2\times10^6$ CFU, $5\times10^6$ CFU, $1\times10^7$ CFU, $2\times10^7$ CFU, $5\times10^7$ CFU, $1\times10^8$ CFU, $2\times10^8$ CFU, $5\times10^8$ CFU, $1\times10^9$ CFU, $2\times10^9$ CFU, $5\times10^9$ CFU, $1\times10^{10}$ CFU, $2\times10^{10}$ CFU, $5\times10^{10}$ CFU, $1\times10^{11}$ CFU, $2\times10^{11}$ CFU, $5\times10^{11}$ CFU, $1\times10^{12}$ CFU, $2\times10^{12}$ CFU, $5\times10^{12}$ CFU, or more or ranges therebetween) of a modified AIEC strain. In some embodiments, the bacterial formulation is administered to the subject in two or more doses (e.g., 2, 3, 4, 5, 6, 7, 8, 9, 10, or more, or ranges therebetween). In some embodiments, the administration of doses are separated by at least 1 day (e.g., 2 days, 3 days, 4 days, 5 days, 6 days, 1 week, 2 weeks, 3 weeks, 4 weeks, or ranges therebetween).

For oral or buccal administration, bacteria of embodiments of the present invention may be combined with various excipients. Solid pharmaceutical preparations for oral administration often include binding agents (for example syrups, acacia, gelatin, tragacanth, polyvinylpyrrolidone, sodium lauryl sulphate, pregelatinized maize starch, hydroxypropyl methylcellulose, starches, modified starches, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone and sodium alginate), disintegrants (such as starch and preferably corn, potato or tapioca starch, alginic acid and certain complex silicates, polyvinylpyrrolidone, gelatin, acacia, sodium starch glycollate, microcrystalline cellulose, crosscarmellose sodium, crospovidone, hydroxypropyl methylcellulose and hydroxypropyl cellulose), lubricating agents (such as magnesium stearate, sodium lauryl sulfate, talc, silica polyethylene glycol waxes, stearic acid, palmitic acid, calcium stearate, carnuba wax, hydrogenated vegetable oils, mineral oils, polyethylene glycols and sodium stearyl fumarate), and fillers (including high molecular weight polyethylene glycols, lactose, calcium phosphate, glycine magnesium stearate, starch, rice flour, chalk, gelatin, microcrystalline cellulose, calcium sulphate, and lactitol). Such preparations may also include preservative agents and anti-oxidants.

Liquid compositions for oral administration may be in the form of, for example, emulsions, syrups, or elixirs, or may be presented as a dry product for reconstitution with water or other suitable vehicle before use. Such liquid compositions may contain conventional additives such as suspending agents (e.g., syrup, methyl cellulose, hydrogenated edible fats, gelatin, hydroxyalkylcelluloses, carboxymethylcellulose, aluminium stearate gel, hydrogenated edible fats) emulsifying agents (e.g., lecithin, sorbitan monooleate, or acacia), aqueous or non-aqueous vehicles (including edible oils, e.g., almond oil, fractionated coconut oil) oily esters (for example esters of glycerine, propylene glycol, polyethylene glycol or ethyl alcohol), glycerine, water or normal saline; preservatives (e.g., methyl or propyl p-hydroxybenzoate or sorbic acid) and conventional flavouring, preservative, sweetening or coloring agents. Diluents such as water, ethanol, propylene glycol, glycerin and combinations thereof may also be included.

Other suitable fillers, binders, disintegrants, lubricants and additional excipients are well known to a person skilled in the art.

In some embodiments, microbes are spray-dried. In other embodiments, microbes are suspended in an oil phase and are encased by at least one protective layer, which is water-soluble (water-soluble derivatives of cellulose or starch, gums or pectins; See e.g., EP 0 180 743, herein incorporated by reference in its entirety).

In some embodiments, the present technology provides kits, pharmaceutical compositions, or other delivery systems for use in treatment (rehabilitative or prophylactic treatment) of enteric inflammation (e.g., gastrointestinal inflammation) in an animal. The kit may include any and all components necessary, useful or sufficient for research or therapeutic uses including, but not limited to, one or more microbes, pharmaceutical carriers, and additional components useful, necessary or sufficient for use in treatment (rehabilitative or prophylactic treatment) of inflammation (e.g., gastrointestinal inflammation) in an animal. In some embodiments, the kits provide a sub-set of the required components, wherein it is expected that the user will supply the remaining components. In some embodiments, the kits comprise two or more separate containers wherein each container houses a subset of the components to be delivered, and/or instructions for use.

Optionally, compositions and kits comprise other active components in order to achieve desired therapeutic effects.

Embodiments of the present technology provide compositions comprising microbes (e.g., modified AIEC strains alone or in combination with additional microbes) (e.g., pharmaceutical, nutraceutical, or food compositions) for use in improving or repairing the health of an animal. In some embodiments, compositions find use for use in treatment (rehabilitative or prophylactic treatment) of inflammation (e.g., gastrointestinal inflammation) in an animal. In some embodiments, the animal is a domestic or agricultural animal (e.g., cow, sheep, goat, pig, etc.). In some embodiments, the animal is neonatal, newborn, or young. For example, in some embodiments, the animal is one day, 2, days, 3, days, 4 days, 5 days, 6 days, 1 week, 2 weeks, 3 weeks, one month, or 2 months of age, although other ages are specifically contemplated.

In some embodiments, compositions comprising microbes (e.g., modified AIEC strains) are administered once to an animal in need thereof.

In some embodiments, compositions comprise prebiotic compounds such as carbohydrate compounds selected from the group consisting of inulin, fructooligosaccharide (FOS), short-chain fructooligosaccharide (short chain FOS), galacto-oligosaccharide (GOS), xylooligosaccharide (XOS), glangliosides, partially hydrolysed guar gum (PHGG) acacia gum, soybean-gum, apple extract, lactowolfberry, wolfberry extracts or mixture thereof. Other carbohydrates may be present such as a second carbohydrate acting in synergy with the first carbohydrate and that is selected from the group consisting of xylooligosaccharide (XOS), gum, acacia gum, starch, partially hydrolysed guar gum or mixture thereof. The carbohydrate or carbohydrates may be present at about 1 g to 20 g or 1% to 80% or 20% to 60% in the daily doses of the composition. Alternatively, the carbohydrates are present at 10% to 80% of the dry composition.

The daily doses of carbohydrates, and all other compounds administered comply with published safety guidelines and regulatory requirements.

In some embodiments, compositions are administered on an ongoing, recurrent, or repeat basis (e.g., multiple times a day, once a day, once every 2, 3, 4, 5, or 6 days, once a week, etc.) for a period of time (e.g., multiple days, months, or weeks). Suitable dosages and dosing schedules are determined by one of skill in the art using suitable methods (e.g., those described in the experimental section below or known to one of skill in the art).

In some embodiments, a single strain of modified AIEC strain bacteria is administered. In some embodiments, a formulation of multiple (e.g., 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, or more, or ranges therebetween) modified AIEC strains are administered.

In some embodiments, modified AIEC strains for administration to a subject are selected from one or more bacteria selected from the class AIEC.

In some embodiments, administration of modified AIEC strains facilitate establishment of beneficial gut microbiota. In some embodiments, administration of modified AIEC strains prevent or decrease susceptibility to infection or colonization by pathogenic or detrimental microbes. For example, in some embodiments, the compositions, methods, kits, etc. herein prevent or decrease susceptibility to infection or colonization by pathogenic AIECs.

In some embodiments, the methods and compositions herein are used to prophylactically prevent infection or colonization with pathogenic or detrimental microbes (e.g., bacteria). In some embodiments, the methods and compositions herein are used to treat inflammation or colonization with pathogenic or detrimental microbes (e.g., bacteria).

II. Methods of Treatment

In some embodiments, a composition comprising a modified AIEC strain is administered to a subject or patient in a pharmaceutically effective amount. In certain embodiments, a composition comprising a modified AIEC strain is administered in a therapeutically effective dose.

The dosage amount and frequency are selected to create an effective level of a modified AIEC strain without substantially harmful effects. When administered (e.g., orally, rectally, etc.), the dosage will generally comprise at least $1\times10^4$ CFU per dose or per day (e.g., $1\times10^4$ CFU, $2\times10^4$ CFU, $5\times10^4$ CFU, $1\times10^5$ CFU, $2\times10^5$ CFU, $5\times10^5$ CFU, $1\times10^6$ CFU, $2\times10^6$ CFU, $5\times10^6$ CFU, $1\times10^7$ CFU, $2\times10^7$ CFU, $5\times10^7$ CFU, $1\times10^8$ CFU, $2\times10^8$ CFU, $5\times10^8$ CFU, $1\times10^9$ CFU, $2\times10^9$ CFU, $5\times10^9$ CFU, $1\times10^{10}$ CFU, $2\times10^{10}$ CFU, $5\times10^{10}$ CFU, $1\times10^{11}$ CFU, $2\times10^{11}$ CFU, $5\times10^{11}$ CFU, $1\times10^{12}$ CFU, $2\times10^{12}$ CFU, $5\times10^{12}$ CFU per dose or per day, or more per dose or per day, including ranges therebetween) of a modified AIEC strain.

Methods of administering a composition comprising a modified AIEC strain (e.g., an effective level of a modified AIEC strain) include, without limitation, administration in oral, intranasal, topical, sublingual, rectal, and vaginal forms.

In some embodiments, a single dose of a composition comprising a modified AIEC strain (e.g., an effective level of a modified AIEC strain) is administered to a subject. In other embodiments, multiple doses are administered over two or more time points, separated by hours, days, weeks, etc. In some embodiments, a composition comprising a modified AIEC strain (e.g., an effective level of a modified AIEC strain) is administered over a long period of time (e.g., chronically), for example, for a period of months or years (e.g., 1, 2, 3, 4, 5, 6, 7, 8, 9, 10, 11, 12, or more months or years; for the subject's lifetime). In such embodiments, a composition comprising a modified AIEC strain (e.g., an effective level of a modified AIEC strain) may be taken on a regular scheduled basis (e.g., daily, weekly, etc.) for the duration of the extended period.

The technology also relates to methods of treating a subject with a composition comprising a therapeutic modified AIEC strain (e.g., an effective level of a modified AIEC strain). In some embodiments, the subject has an enteric inflammation (e.g., gastrointestinal inflammation). In some embodiments, the subject does not have an enteric inflammation (e.g., gastrointestinal inflammation) and the composition comprising a modified AIEC strain (e.g., an effective level of a modified AIEC strain) is administered to prevent enteric inflammation (e.g., gastrointestinal inflammation) or reduce the risk of the subject having enteric inflammation (e.g., gastrointestinal inflammation).

Accordingly, in some embodiments of the technology, a method is provided for treating a subject in need of such treatment with a composition comprising a therapeutic modified AIEC strain (e.g., an effective level of a modified AIEC strain). The method involves administering to the subject a composition comprising a modified AIEC strain (e.g., an effective level of a modified AIEC strain) in any one of the pharmaceutical preparations described above, detailed herein, and/or set forth in the claims. The subject can be any subject in need of such treatment. It should be understood, however, that the composition comprising a modified AIEC strain (e.g., an effective level of a modified AIEC strain) is a member of a class of compositions and the technology is intended to embrace pharmaceutical preparations, methods, and kits containing related derivatives within this class. Another aspect of the technology then embraces the foregoing summary but read in each aspect as if any such derivative is substituted wherever "composition" appears.

III. Testing

In some embodiments, the present invention provides compositions and methods for research, screening, and diagnostic applications. For example, in some embodiments, diagnostic applications provide a risk or a measure of intestinal health. In some embodiments, the level, presence or absence of a modified AIEC strain, is used to provide a diagnosis or prognosis. For example in some embodiments, a lack of or decreased level of a modified AIEC strain is associated with an increased risk of decreased gastrointestinal health.

In some embodiments, subjects are tested. Exemplary diagnostic methods are described herein. In some embodiments, intact bacteria are detected (e.g., by detecting surface polypeptides or markers). In other embodiments, bacteria are lysed and nucleic acids or proteins (e.g., corresponding to genes specific to the species of bacteria) are detected.

In some embodiments, bacteria are identified using detection reagents (e.g., a probe, a microarray, e.g., an amplification primer) that specifically interact with a nucleic acid that identifies a particular species of bacteria (e.g., a modified AIEC strain).

Some embodiments comprise use of nucleic acid sequencing to identify gut microbiota and/or to detect a modified AIEC strain. The term "sequencing," as used herein, refers to a method by which the identity of at least 10 consecutive nucleotides (e.g., the identity of at least 20, at least 50, at least 100, or at least 200 or more consecutive nucleotides) of a polynucleotide are obtained. The term "next-generation sequencing" refers to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies.

Some embodiments of the technology comprise acquiring a gut microbiota sample from a subject. As used herein, "gut microbiota sample" refers to a biological sample comprising a plurality of heterogeneous nucleic acids produced by a subject's gut microbiota. Fecal samples are commonly used in the art to sample gut microbiota. Methods for obtaining a fecal sample from a subject are known in the art and include, but are not limited to, rectal swab and stool collection. Suitable fecal samples may be freshly obtained or may have been stored under appropriate temperatures and conditions known in the art. Methods for extracting nucleic acids from a fecal sample are also well known in the art. The extracted nucleic acids may or may not be amplified prior to being used as an input for profiling the relative abundances of bacterial taxa, depending upon the type and sensitivity of the downstream method. When amplification is desired, nucleic acids may be amplified via polymerase chain reaction (PCR). Methods for performing PCR are well known in the art. Selection of nucleic acids or regions of nucleic acids to amplify are discussed above. The nucleic acids comprising the nucleic acid sample may also be fluorescently or chemically labeled, fragmented, or otherwise modified prior to sequencing or hybridization to an array as is routinely performed in the art.

In certain embodiments, the sample sequenced may comprise a pool of nucleic acids from a plurality of samples, wherein the nucleic acids in the sample have a molecular barcode to indicate their source. In other embodiments the nucleic acids being analyzed may be derived from a single source (e.g., from different sites or a time course in a single subject), whereas in still other embodiments, the nucleic acid sample may be a pool of nucleic acids extracted from a plurality of different sources (e.g., a pool of nucleic acids from different subjects), where by "plurality" is meant two or more. Molecular barcodes may allow the sequences from different sources to be distinguished after they are analyzed.

In some embodiments, gut microbiota samples are obtained from a subject (e.g., a healthy subject or a not healthy subject (e.g., a patient or a subject in need of treatment according to the technology provided herein) at any suitable interval of time, varying from minutes to hours apart, days to weeks apart, or even weeks to months apart. Gut microbiota samples may be obtained multiple times a day, week, month or year. The duration of sampling can also vary. For example, the duration of sampling may be for about a month, about 6 months, about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 30 years, or more.

In some embodiments, subjects identified as being at increased risk of decreased intestinal health are administered compositions (e.g., comprising a modified AIEC strain) described herein.

In some embodiments, a subject is tested to assess the presence, the absence, or the level of a modified AIEC strain in the gut microbiota. In some embodiments, a subject is tested to assess the presence, the absence, or the composition (e.g., membership, relative abundance, etc.) of the gut microbiota. In some embodiments, a subject is tested to assess the presence, the absence, or the level of a pathogenic organism. In some embodiments, a subject is tested to assess the presence, the absence, or the level of a pathogenic organism in the gut microbiota.

Such testing is performed, e.g., by assaying or measuring a biomarker (e.g., a nucleic acid, e.g., a rRNA gene), a metabolite, a physical symptom, an indication, etc.

In some embodiments, a quantitative score is determined, e.g., the relative abundance of a modified AIEC strain and/or the relative abundance of a pathogenic organism.

In some embodiments, testing is related to testing for a condition such as enteric inflammation (e.g., gastrointestinal inflammation) or risk of enteric inflammation (e.g., gastrointestinal inflammation).

In some embodiments, the subject is treated with a composition comprising a modified AIEC strain (e.g., an effective level of a modified AIEC strain) based on the outcome of the test. Accordingly, in some embodiments, a subject is tested and then treated based on the test results. In other embodiments, a subject is treated and then tested to assess the efficacy of the treatment. In some embodiments, a subsequent treatment is adjusted based on a test result, e.g., the dosage amount, dosage schedule, composition administered, etc. is changed. In certain embodiments, a patient is tested, treated, and then tested again to monitor the response to therapy and/or to change the therapy. In further embodiments, cycles of testing and treatment may occur without limitation to the pattern of testing and treating (e.g., test/treat, treat/test, test/treat/test, treat/test/treat, test/treat/test/treat, test/treat/test/treat/test, test/treat/test/test/treat/treat/treat/test, test/treat/treat/test/treat/treat, etc.), the periodicity, or the duration of the interval between each testing and treatment phase.

EXPERIMENTAL

Results

Bacterial Dysbiosis Induced by Antibiotic Treatment Enhances DSS-Induced Colitis in the Absence of IL-22

We used a chemically-induced colitis model in which oral administration of dextran sulfate sodium (DSS) triggers epithelial damage and inflammation to investigate the role of the microbiota in colitis. To address the role of dysbiosis-associated colitis in the immunocompromised host, we used mice lacking IL-22, a cytokine that is important for immune protection at the intestinal barrier [25]. WT and $Il22^{-/-}$ mice were pretreated with a cocktail of antibiotics for 6 days to induce dysbiosis prior to the administration of DSS. We assessed colitis by measuring body weight, colon length, histopathology and fecal lipocalin-2 (Lcn2), a marker of intestinal inflammation [26]. We found that $Il22^{-/-}$ mice pretreated with antibiotics showed more weight loss, more shortening of colon length, and greater fecal lipocalin-2 levels after DSS treatment than WT mice pretreated with antibiotics, and untreated WT or $Il22^{-/-}$ mice (FIG. 1A to C). Consistent with these findings, higher pathology scores were found in the intestine of antibiotic-pretreated $Il22^{-/-}$ mice than in antibiotic-treated WT mice and untreated mice (FIGS. 1D, E, and 6A). These results indicate that antibiotic-induced dysbiosis exacerbates DSS-induced colitis in the absence of IL-22.

To determine how antibiotic treatment affects the microbiota during DSS-induced colitis, we analyzed the composition of the microbiota using Illumina MiSeq® 16S rRNA gene sequencing. Consistent with previous studies [6, 27], treatment of $Il22^{-/-}$ and WT mice with a cocktail of 7 antibiotics resulted in an increased abundance of Enterobacteriaceae before and after treatment with DSS (FIG. 1F). The dominance of Enterobacteriaceae in antibiotic-treated $Il22^{-/-}$ and WT mice was accompanied by an increase in Bacteroidaceae after DSS treatment (FIG. 1F). We confirmed that antibiotic treatment increases the abundance of Enterobacteriaceae in both $Il22^{-/-}$ and WT mice by quantitative PCR using specific primers (FIG. 6B). To identify bacteria associated with colitis, we determined the most dominant bacteria that are associated with increased fecal Lcn2 levels by Spearman ranking correlation analysis. We found that *Escherichia* was the most abundant genera associated with increased Lcn2 levels in the intestine (Spearman's ranking correlation coefficient=0.449, $p<0.0014$, average abundance=16.2%) (FIG. 1G). These results indicate that the blooming of certain Enterobacteriaceae species including *E. coli* is associated with antibiotic-induced dysbiosis in WT and IL-22-deficient mice. Furthermore, IL-22 protects the host from dysbiosis-associated colitis in DSS-treated animals.

Colitis-Associated *E. coli* Isolates Belong to AIEC

To determine the role of Enterobacteriaceae that accumulate during antibiotic-induced dysbiosis in colitis, we isolated Enterobacteriaceae species from the intestine of antibiotic-treated $Il22^{-/-}$ mice. Consistent with previous studies [27], bacteria belonging to *Enterobacter* and *Escherichia* were identified as dominant Enterobacteriaceae genera that bloom after treatment with antibiotics. To determine the role of the bacterial species in colitis, we isolated *E. coli* as the most abundant bacteria associated with increased Lcn2 levels in the intestine (FIG. 1G), and determined full genomic sequences of four independent *E. coli* isolates, NI1429, NI1413, NI1423 and NI1522. Analysis of their genomes showed that all of four strains belong to the B2-phylogroup ($ChuA^+YjaA^+TSPE4.C2^-$) which is common in human AIEC strains [13]. Furthermore, the four *E. coli* strains were genetically similar and showed high similarity to human AIEC strains when compared to ~600 reference *E. coli* strains by Roary (FIG. 7A). The four mouse *E. coli* isolates and human AIEC reference strains showed high homology in protein sequences (>91%) and their genomes contained a unique set of ~340 genes not found in the reference *E. coli* laboratory strain K-12 MG1655. These genes conserved in mouse and human AIEC strains include many putative virulence genes (FIG. 7B). In addition, the genomes of mouse AIEC isolates harbor genes encoding type I fimbrial proteins, invasin-like adhesins and strain-specific flagella. The polymorphisms of type I fimbrial protein FimH in the mouse isolates were identical to those reported to be important for adhesiveness and invasiveness in human AIEC [13]. These results indicate that *E. coli* isolated from colitic $Il22^{-/-}$ mice possess genetic features that are characteristic of human AIEC.

Figure 2:
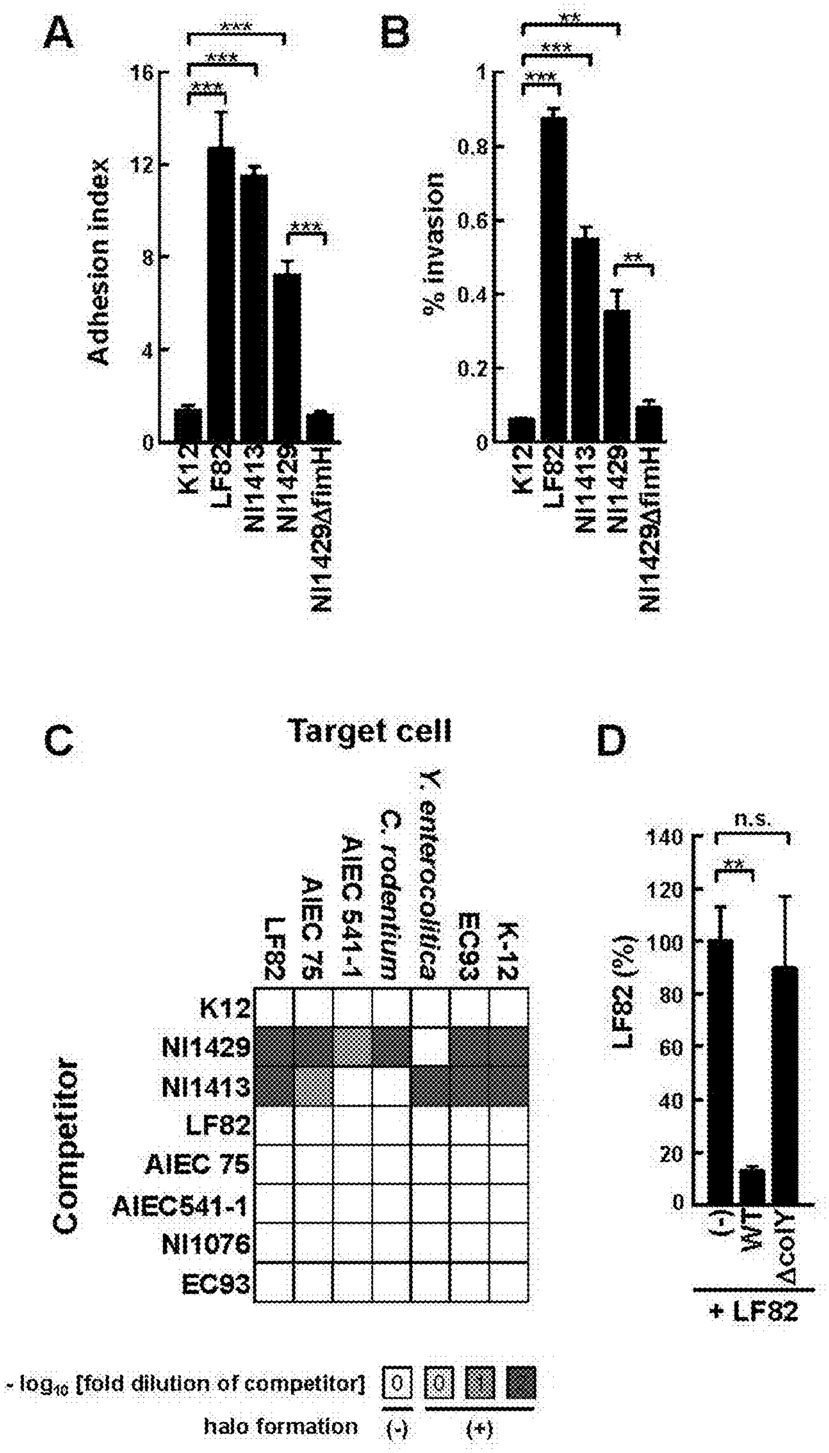
FIG. 2. Colitis-associated *E. coli* isolates have AIEC features and possess high ability to outcompete related bacteria.

The genetic evidence that colitis-associated *E. coli* mouse isolates exhibit multiple features of AIEC prompted investigation of whether these bacterial strains exhibit phenotypes characteristic of AIEC. To determine if the mouse *E. coli* isolates function as AIECs, we performed adhesion and invasion assays using T84 intestinal epithelial cells as described [28]. The colitis-associated *E. coli* isolates, NI1413 and NI1429 demonstrated the ability to adhere to and invade into T84 intestinal epithelial cells (FIGS. 2A and B). To verify the role of Fim type I fimbrial adherence in the AIEC phenotype, we deleted fimH in one of the mouse isolates by homologous recombination. Consistent with the important role of the type I fimbriae in the AIEC phenotype of the human LF82 strain [13], the adhesiveness and invasiveness of NI1429 was lost after deletion of fimH (FIGS. 2A and B). These results indicate that the murine isolates are AIECs.

Colitis-Associated AIEC Possess High Ability to Outcompete Symbiotic Bacteria

Further evaluation of bacterial genomes of colitis-associated *E. coli* isolates revealed that they contain putative genes involved in inter-species competition. These include genes for the production of colicins on plasmids, type VI secretion system (T6SS) effectors and factors for contact-dependent growth inhibition (FIG. 7B). These findings indicate that colitis-associated *E. coli* isolates have potential to outcompete other bacteria and acquire dominance under dysbiotic conditions. Because all four colitis-associated *E. coli* isolates contained plasmid-encoded colicins that act as antimicrobial peptides against competitive bacteria [29], we performed halo assays to determine the ability of the isolates to outcompete other enterobacteria by overlaying the competitors on target bacteria [29]. We found that two colitis-associated *E. coli* strains, NI1413 and NI1429, exhibited potent ability to outcompete other *E. coli* strains and related enterobacteria, including human AIECs and the mouse pathogen *C. rodentium* (FIG. 2C). To further characterize the role of colicins in bacterial competition, we deleted colY, a colicin gene in NI1429, a representative mouse AIEC isolate. In these experiments, we co-cultured ampicillin-resistant strain LF82, a reference human AIEC strain with streptomycin-resistant NI1429 derivatives (NI1429Str) including WT or an isogenic ΔcolY mutant. Consistent with the results of the halo assay, WT NI1429Str exhibits robust ability to inhibit the growth of LF82 and the inhibitory activity is dependent on the presence of colicin Y (FIG. 2D). These results indicate that colitis-associated *E. coli* are AIEC with high competitive ability against related enterobacteria.

Intestinal AIEC Colonization is Regulated by the Surface Polysaccharide Layer and IL-22 Under Colitic Conditions A genetic feature of disease-associated *E. coli* strains is the presence of particular O- and K-serotypes, which reflect differences in the surface polysaccharide layer composed of lipopolysaccharides (LPS) and capsular polysaccharides (CPS), respectively. Both LPS and CPS provide resistance against complement-mediated defense mechanisms [4], and thus colitis-associated *E. coli* strains have the potential to be virulent in the host. In silico serotyping by Serotypefinder and BLAST showed that the serotypes of colitis-associated *E. coli* NI1429 and NI1522 were O54-like: K-:H45, whereas that of NI1413 was O7:K1:H7. To test whether the lipopolysaccharide O structure is important for sensitivity to complement and engulfment by phagocytes, we generated an isogenic mutant strain of NI1429 lacking the surface polysaccharide layer by deletion of the wzy gene (Δwzy) by homologous recombination and its plasmid-complemented strain (Δwzy+wzy) [30, 31]. Biochemical analysis confirmed that the wzy mutant lacks O-antigen of LPS and its complementation with a wzy plasmid restores O-antigen expression (FIG. 8A). Furthermore, the wzy mutant grew at a comparable rate to the WT strain in vitro, and its inhibitory activity against LF82 remained intact (FIGS. 8B and 8C). To assess the C3 binding ability, we compared C3-deposition levels on the *E. coli* NI1429 strain after incubation with fresh mouse serum as a source of C3. K-12 and NI1076 were used as complement sensitive and resistant controls, respectively [6]. Consistent with previous studies [32, 33], the wzy AIEC mutant conjugated more C3 than the parental WT strain and the wzy complemented mutant strain (FIGS. 3A and B). Furthermore, the wzy mutant showed increased engulfment by bone marrow-derived macrophages and susceptibility to killing by peritoneal neutrophils compared with the WT strain (FIG. 3C and D). In addition, the wzy mutant showed reduced ability to adhere to and invade intestinal epithelial cells in vitro compared with the WT strain (Figure S3D and E). These results indicate that the surface polysaccharide layer, which depends on wzy, is critical for resistance to complement and phagocyte killing in colitis-associated *E. coli.*

Next, we tested if the wzy mutant is sensitive to host elimination during colitis in vivo. To this end, we pre-treated the mice with streptomycin for 1 day to deplete the microbiota, and then co-inoculated the mice orally with an equal mixture of streptomycin-resistant WT NI1429 and its isogenic Δwzy mutant strain. In the absence of DSS treatment, the fitness of the Δwzy mutant to colonize the gut decreased less than one log in mock-treated mice, compared with the WT strain (FIG. 3E). In contrast, the colonization fitness of the Δwzy mutant decreased ~3 logs compared with the WT strain after 7 days of DSS treatment (FIG. 3E). Furthermore, the competitive index of the Δwzy mutant improved in $Il22^{-/-}$ mice after DSS treatment when compared with that observed in DSS-treated WT mice (FIGS. 3E and 9A). Previous studies showed that IL-22 limits the systemic colonization of bacterial symbionts through the regulation of the complement system [6]. We found that IL-22 mRNA levels were increased in the colon of DSS-treated WT mice (FIG. 9B). Quantitative RT-PCR and immunoblotting analyses showed increased levels of C3 mRNA in the liver and C3 protein in serum of DSS-treated WT mice (FIG. 9C and D). Consistent with previous studies [6], induction of C3 mRNA in the liver and C3 protein in the serum was largely dependent on IL-22 in DSS-treated mice (FIG. 9C and D). These results indicate that the Δwzy mutant AIEC exhibits reduced ability to colonize the intestine under colitic conditions, and indicate that IL-22 limits the colonization of the Δwzy mutant in the inflamed intestine.

The wzy AIEC Mutant Alleviates DSS-Induced Colitis

We next assessed whether the Δwzy mutant AIEC is protective against intestinal inflammation. To test this, we pretreated with streptomycin for 1 day and then inoculated the mice orally with streptomycin-resistant WT or Δwzy mutant NI1429 strains in the presence of DSS in the drinking water for 7 days. The colonization levels of the WT strain and the Δwzy mutant strain were comparable after 1, 3 and 7 days of DSS treatment (FIG. 4A). Furthermore, mice colonized with the WT bacterium and the Δwzy mutant showed comparable weight loss early after DSS treatment, but mice colonized with the Δwzy mutant showed reduced weight loss after 7 days of DSS treatment (FIG. 4B). The reduced weight loss in mice colonized with the Δwzy mutant was associated with decreased colon shortening and pathology scores when compared with mock-treated or mice colonized with the WT strain (FIGS. 4C to E, and 10A). Analysis of bacterial loads showed increased numbers of the WT NI1429 strain compared with the isogenic Δwzy mutant strain in the mesenteric lymph nodes (FIG. 10B). These results indicate that the lipopolysaccharide O side chain of AIEC regulates intestinal inflammation.

Host Protection Against Colitis by the wzy Mutant Depends on Complement C3

We first examined whether the protective ability of the *E. coli* Δwzy mutant against DSS-induced colitis was associated with changes in the immune populations of the lamina propia in the large intestine. Mice colonized with the Δwzy mutant and mock contained similar numbers of monocytes, macrophages, neutrophils and dendritic cells in the intestinal tissue after DSS treatment (FIG. 11). To determine whether reduced colitis associated with colonization by the Δwzy mutant depends on C3, we depleted C3 in WT B6 mice by intraperitoneal administration of cobra venom factor (CVF) [34]. C3 depletion was confirmed by immunoblotting analysis (FIG. 12A), and macrophage engulfment assay that relies on C3 (FIG. 12B). Importantly, treatment with CVF blocked the ability of the Δwzy mutant to protect against DSS-induced colitis as assessed by weight loss, colon length and pathology scores (FIG. 5A to D, and 12C). To determine if C3 mediates the protective role of the Δwzy mutant against colitis by regulating bacterial numbers, we assessed the colonization levels of the Δwzy mutant bacterium over time after DSS treatment. After C3 depletion, the loads of the Δwzy mutant were ~50-fold higher in mice treated with CVF than in mock-treated mice after 7 days of DSS treatment (FIG. 5E). In contrast, the intestinal loads of the Δwzy mutant was comparable after 1 and 3 days of DSS treatment in the presence and absence of C3 depletion. These results indicate that the anti-inflammatory effect of the Δwzy mutant is dependent on the host complement system.

These results indicate that $Il22^{-/-}$ mice exhibit increased susceptibility to DSS-induced colitis in the presence of antibiotic-induced dysbiosis. Treatment of mice with multiple antibiotics induced accumulation of particular bacterial strains belonging to the Enterobacteriaceae family that include AIEC. Such bacteria exhibited unique genetic traits including the presence of polymorphisms of type I fimbriae tip adhesin FimH, genes producing T6SS effectors, genes associated with anti-bacterial immunity such as colicin-containing plasmids and genes for contact-dependent growth inhibition. While colonization of mice with WT AIEC did not exacerbate DSS-induced colitis, an AIEC mutant deficient in wzy that encodes an enzyme responsible for the biosynthesis of the surface polysaccharide layer, surprisingly conferred protection against intestinal inflammation and colitis. Resistance of bacteria to host defense responses is dependent, at least in part, on structures present on the bacterial surface and in particular O- and K-serotypes expressed by enterobacteria [4]. In pathogenic enterobacteria, these polysaccharide structures are associated with bacterial virulence and fitness at invasion sites [35, 36]. We observed that the protective function of surface polysaccharide synthesized by wzy is primarily found under inflamed conditions, suggesting a role for host immune factors in the regulation of wzy-dependent bacterial fitness. Previous work showed that O- and K-serotypes are important for virulence and resistance to host elimination in ExPEC including uropathogenic and neonatal meningitis-associated *E. coli* [37-39]. However, the role of surface polysaccharides of intestinal commensal pathogenic *E. coli* (InPEC), including AIEC, in the regulation of intestinal colonization has not been previously identified. Our findings indicate that the sensitivity of an InPEC strain such as NI1429 to complement is critical for regulation of disease activity in the intestine. Consistent with this determination, the loss of surface polysaccharides by the wzy deficiency in AIEC alleviates the susceptibility to intestinal inflammation and colitis. Mutations potentially acquired during the generation of streptomycin-resistant *E. coli* strains could contribute to the protective phenotype in vivo. Probiotic Nissle 1917, a human *E. coli* strain, which has been widely used as a non-pathogenic, non-AIEC probiotic strain has a wzy mutation [32]. Nissle 1917 produces microcins H47 and M which has been suggested to mediate its ability to outcompete other bacteria and reduce colitis [40, 41]. Contrary to probiotic, non-AIEC strains, our evidence shows that the ability of modified AIEC strains to outcompete other bacteria via the production of colicins under colitic conditions may be harnessed for the generation of therapeutic modified AIEC strains. Because such mutants occupy the same ecological niche that WT AIEC and related bacteria inhabit, replacement of pro-inflammatory WT bacteria with mutant AIEC strains such as those harboring the wzy mutation is beneficial in reducing inflammatory activity. Non-AIEC, probiotic Nissle1917 may outcompete other bacteria through diverse mechanisms [41-44] that may further be shared with modified/mutant AIEC strains.

These data indicate that the protective function of the wzy mutant against intestinal inflammation and colitis depends in part on C3. Depletion of C3 results in an increased abundance of *E. coli* in the intestine of DSS-treated, but not untreated mice, indicating that C3 regulates the number of *E. coli* in the intestine only under colitic conditions. Because C3 can be found in intestinal contents [45, 46], the effect of C3 to regulate *E. coli* abundance may be mediated by C3 released into the intestinal lumen, although claims of the present invention are not limited to one mechanism or to any mechanism. Several approaches using non-AIEC, probiotic bacteria have been proposed for the treatment of IBD [47]. These include the use of bacterial strains such as non-AIEC Nissle 1917 that were selected by functional screens for effectiveness in clinical trials. Non-AIEC Nissle 1917 has been used to promote the maintenance of remission in UC patients [48]. Our findings demonstrate that the therapeutic benefits of the wzy mutant of colitis-associated AIEC NI1429 may rely in part on host immune factors including C3, indicating that effective use of a modified AIEC strains based on the wzy mutation also may rely in part on the presence of a normal immune system, and in particular on an intact complement system. Although the beneficial effect of the Δwzy mutant AIEC strain may rely in part on an intact complement system, the precise mechanism is not yet known, and is not necessary to make or to practice the present invention. For example, complement-sensitive bacteria with a high capacity to outcompete other bacteria may decrease pro-inflammatory bacteria, and enable the host to eliminate translocated bacteria via C3.

Targeted Deletion of wzy of LF82 and GT of NI1429

Targeted deletion of wzy of LF82 and GT of NI1429 was performed by homologous recombination using the pKD46 system as described [63]. Briefly, NI1429 was transformed with pKD46, and the chromosomal genes were replaced by a chloramphenicol resistance cassette from the plasmid pKD3 plasmid using a PCR fragment amplified with primers:

LF82 wzy 5:
TTAGAGAAAATTTTCCTTCAACATTATC-TACTAAAATAATAAAATCATGAgtgtaggctgga gctgcttc, (SEQ ID NO: 29)
LF82 wzy 3:
TCTCAGGTCTACCAAAGGTAGGGATAACTATT-GATACTTTAATATTCATATATATAT CCTCCcatat-gaatatcctcctta, (SEQ ID NO: 30)
NI1429 GT 5:
TTTTCCGTATTTATTTATACGTTGATTCT-TATCCGGGGGGTACTTGCACTgtgtaggctggag ctgcttc (SEQ ID NO: 31)
NI1429 GT 3:
GTATTACGTGAATAAAGAGTGTAGCAAACATCTA-CAACCGCTTTTTTCATACAATCC TCTTcatat-gaatatcctcctta. (SEQ ID NO: 32)

The chloramphenicol (Kan) resistance cassette was removed using the pCP20 plasmid. Deletion of the target gene and the removal of Cm gene was confirmed by PCR.

C3 deposition Western blotting assays were performed as described. Briefly, $5\times10^8$ bacteria were incubated in 50% (v/v) mouse serum for 30 min at 37° C. Unbound C3 was removed from bacterial pellets by washing with ice-cold PBS. Samples and control 1/200 total reaction mixtures were boiled in Laemmli's buffer, separated by 10% SDS-PAGE ($1\times10^8$ bacteria per lane). For C3 deposition, C3 protein was examined by immunoblotting using anti-mouse C3d antibody (R&D). For equal loading, bacterial aliquots from each sample were plated and the same number of CFUs were lysed. As shown in FIG. 13(A), in bacteria present in humans, the mutation is associated with increased complement deposition on the bacterial surface. These results indicate that methods and compositions of the present invention generate mutant bacteria of utility in treating intestinal inflammation in humans. As shown in FIG. 13(B), inactivation of another gene in the shared metabolic pathway (i.e., GT, glycosyltransferase in the lipoploysaccaride O synthetic pathway) regulates complement deposition. These results indicate that inactivation of constituents in a shared metabolic pathway other than wzy generates of bacteria of clinical utility.

Materials and Methods

Abbreviations. Abx, antibiotics; AIEC, adherent-invasive *Escherichia coli*; CD, Crohn's disease; CFU, colony-forming units; CPS, capsular polysaccharides; CVF, cobra venom factor; DSS, dextran sulfate sodium; *E. coli, Escherichia coli*; ExPEC, extraintestinal pathogenic *E. coli*; IBD, inflammatory bowel disease; LDA, linear discriminant analysis; LEfSe, linear discriminant analysis effect size; LPS, lipopolysaccharides; NMDS, non-metric multidimensional scaling; OTU, operational taxonomic units; qPCR, quantitative polymerase chain reaction; UC, ulcerative colitis; WT, wild type.

Reagents and culture cells. Fc-IL-22 was obtained from AdipoGen® LIFE SCIENCE (San Diego, CA). Cobra venom factor (CVF) was purchased from Complement Technology (Tyler, TX). Human intestinal epithelial T84 cells were obtained from ATCC, cultured and maintained with DMEM/F12 (1:1) medium (Thermo Fischer Scientific, Waltham, MA) supplemented with 10% fetal bovine serum and 1% penicillin-streptomycin.

Mice. WT C57BL/6 mice were obtained from the Jackson Laboratory. $Il22^{-/-}$ mice on C57BL/6 background were a gift from Dr. Wenjun Ouyang (Genentech). All mice were housed, bred, and maintained under specific pathogen-free conditions as described in Hasegawa et al. [6] Mice in different cages were cohoused for 3 weeks for normalization of the microbiota before the experiments. The mouse studies were approved by the University of Michigan Committee on Use and Care of Animals (approved protocol #PRO00008086).

Bacterial strains, isolation, culture, and mutagenesis of bacteria. All strains and plasmids used in this study are listed in Table 1.

TABLE 1

*E. coli* strains and plasmids used in this study

| Strains and plasmids | Description<br>Source and reference |
|---|---|
| *E. coli* | |
| K-12 substr. MG1655 | Non-pathogenic commensal. Complement-sensitive control<br>ATCC |
| NI1076 infected with | Mouse ExPEC strain isolated from liver of $Il22^{-/-}$ mice<br>[1]<br>*Clostridium difficile*. |
| LF82 | AIEC reference strain<br>[2] |
| NI1396 | isolate from feces of $Il22^{-/-}$ mice 7 days after DSS-treatment<br>This study |
| NI1413 | isolate from feces of $Il22^{-/-}$ mice 7 days after DSS-treatment<br>This study |
| NI1423 | isolate from feces of $Il22^{-/-}$ mice 7 days after DSS-treatment<br>This study |

TABLE 1-continued

E. coli strains and plasmids used in this study

| Strains and plasmids | Description<br>Source and reference |
|---|---|
| NI1522 | isolate from feces of $Il22^{-/-}$ mice 7 days after DSS-treatment<br>This study |
| NI1429 | isolate from feces of $Il22^{-/-}$ mice 7 days after DSS-treatment<br>This study |
| NI1429Str | $Str^r$ strain of NI1429<br>This study |
| NI1429StrDwzy::Cm | NI1429str with wzy gene replaced with CAT cassette<br>This study |
| NI1429StrDwzy | NI1429str with wzy gene deleted<br>This study |
| NI1429StrDwzy[pGEM-T-wzy] | complemented strain of NI1429str Dwzy<br>This study |
| NI1429strDfimH::Cm | NI1429str with fimH gene replaced with CAT<br>This study |
| NI1429strDfimH | NI1429str with fimH gene deleted<br>This study |
| NI1429Str[pNI1429Amp] | NI1429str carrying pNI1429Amp<br>This study |
| NI1429Str[pNI1429AmpDcol] | NI1429str carrying pNI1429AmpDcol<br>This study |
| NI1159 | isolate from feces of *C. difficile*-infected $Il22^{-/-}$ mice<br>[1] |
| NI1163 | isolate from feces of *C. difficile*-infected $Il22^{-/-}$ mice<br>[1] |
| NI1165 | isolate from feces of *C. difficile*-infected $Il22^{-/-}$ mice<br>[1] |
| NI491 | mouse commensal strain<br>[1] |
| NI491Str | $Str^r$ strain of NI491<br>[1] |
| Plasmids | |
| pKD3 | Plasmid with FRT-flanked chloramphenicol-resistant gene<br>[3] |
| pKD46 | Plasmid expressing lRed recombinase system<br>[3] |
| pCP20 | Plasmid expressing FLP recombinase<br>[3] |
| pGEM-T-wzy | pGEM-T carrying a 10.7 kb fragment of wzy gene of NI1429<br>This study |
| pNI1429 | Endogenous plasmid in NI1429<br>This study |
| pNI1429Amp | Plasmid carrying ampicillin-resistant gene<br>This study |
| pNI1429AmpDcol | Colicin Y deletion mutant of the plasmid pNI1429<br>This study |

References:
[1] Hasegawa M, Yada S, Liu M Z, Kamada N, Munoz-Planillo R, Do N, et al. Interleukin-22 regulates the complement system to promote resistance against pathobionts after pathogen-induced intestinal damage. Immunity. 2014; 41(4): 620-32. doi: 10.1016/j.immuni.2014.09.010. PubMed PMID: 25367575; PubMed Central PMCID: PMCPMC4220303.
[2] Darfeuille-Michaud A, Boudeau J, Bulois P, Neut C, Glasser A L, Barnich N, et al. High prevalence of adherent-invasive *Escherichia coli* associated with ileal mucosa in Crohn's disease. Gastroenterology. 2004; 127(2): 412-21. PubMed PMID: 15300573.
[3] Datsenko K A, Wanner B L. One-step inactivation of chromosomal genes in *Escherichia coli* K-12 using PCR products. Proc Natl Acad Sci USA. 2000; 97(12): 6640-5. doi: 10.1073/pnas.120163297. PubMed PMID: 10829079; PubMed Central PMCID: PMCPMC18686.

Fecal bacteria were isolated by plating on non-selective bovine heart infusion medium at 37° C. under aerobic conditions, further selected by plating on MacConkey medium, and stored with 25% glycerol at −40° C. until experiments. Bacterial species were determined by sequencing 16S rRNA genes as described [6]. *E. coli* K-12 substr. MG1655 and *Yersinia enterocolitica enterocolitica* ATCC 27729 were obtained from ATCC. *E. coli* LF82, AIEC75 and EC93, and *Citrobacter rodentium* DBS120 are gifts of Drs. Tonyia Eaves-Pyles (University of Texas), Kenneth Simpson (Cornell University), Christopher Heynes (University of California), and David Schauer (Massachusetts Institute of Technology), respectively. For experiments, all bacteria were thawed and grown in Miller Luria-Bertani (LB) medium at 37° C. under aerobic conditions.

Spontaneous streptomycin (Str)-resistant strains were generated by successive culture of bacteria on BHI medium containing increasing concentrations (25, 50, 200, 1000, 2000 μg/ml) of streptomycin as described [49]. After cloning candidates, we verified that their growth rates and maximal growth densities were similar to those of the parental strains. Targeted deletion of fimH and wzy of NI1429 was performed by homologous recombination using the pKD46 system as described [50]. NI1429 was transformed with pKD46 and then the chromosomal genes were replaced by a chloramphenicol resistance cassette from the plasmid pKD3 plasmid using a PCR fragment amplified with primers shown in Table 2.

TABLE 2

PCR primers used in this study

| Primer | Purpose | Sequence | SEQ ID NO: |
|---|---|---|---|
| 1429WzyD5 | Mutagenesis | AAAAAAATGCTTATGGTCAGTACTTAATC AAATTGACACAGGGATAATAAGTGTAGGC TGGAGCTGCTTC | 1 |
| 1429WzyD3 | Mutagenesis | TTCTGAGGTAGATCTCCGTTATAGACACT CATAATAACAGCTATCTTGTCCATATGAA TATCCTCCTTA | 2 |
| D-Eco1429-FimH Fw | Mutagenesis | ACAGCTGAACCCGAAGAGATGATTGTAAT GAAACGAGTTATTACCCTGTTTGCTGTAG GCTGGAGCTGCTTCG | 3 |
| D-Eco1429-FimH Rv | Mutagenesis | CAGCATTAGCAATGTCCTGTGATTTCTTT ATTGATAAACAAAAGTCACGCCAATCATA TGAATATCCTCCTTAG | 4 |
| 1429WzyC5 | Genotyping | AATTGAAGAGCGTCAGGGGC | 5 |
| 1429WzyC-WT3 | Genotyping | GTTGCCAGTGCTTGCCTTAC | 6 |
| CmCassetteC3 | Genotyping | GGCAATGAAAGACGGTGAGC | 7 |
| FimH common 5 | Genotyping | CATTCAGGCAGTGATTAGCATC | 8 |
| FimH WT 3 | Genotyping | GATAACACGCCGCCATAAGC | 9 |
| FimH-Cm mutant 3 | Genotyping | GGCGTGTTACGGTGAAAACC | 10 |
| WzyCompS | Complementation | TGATATCAGGGATAATAAATGGAATCTCT A | 11 |
| WzyCompA | Complementation | GTCGACTTATACCTCGGTATCTAAATAAA TG | 12 |
| Amp5Bam | Plasmid construction | GGGGATCCGGAGATCTCCCGATCCGTC | 13 |
| Amp3 XhoI | Plasmid construction | CCGGGAATTCTAGAAGATCCTTTGATCTT TTCT | 14 |
| Y5Bam | Plasmid genotyping | AAGGATCCTGGTGTTGGTCACCTCTGGA | 15 |
| Y3Xba | Plasmid genotyping | AACCCGGGTCTAGATTCGCTGTGTCCACA TC | 16 |
| ColY5 | ColY genotyping | GCTTCTGTCAATAAACTGATGGCTAATC | 17 |
| ColY3 | ColY genotyping | AAACTTATTCCCCATATCCTCTGCATCA | 18 |
| UniF340 | qPCR | ACTCCTACGGGAGGCAGCAGT | 19 |
| UniR514 | qPCR | ATTACCGCGGCTGCTGGC | 20 |
| Eco1457F | qPCR | CATTGACGTTACCCGCAGAAGAAGC | 21 |
| Eco1652R | qPCR | CTCTACGAGACTCAAGCTTGC | 22 |
| mGapdhS | qPCR | CCCTTAAGAGGGATGCTGCC | 23 |
| mGapdhA | qPCR | TACGGCCAAATCCGTTCACA | 24 |
| mIL-22S | qPCR | GCTCAGCTCCTGTCACATCA | 25 |
| mIL-22A | qPCR | AGCTTCTTCTCGCTCAGACG | 26 |
| mC3S | qPCR | GGGCTGTTAAATGGTTGATTCTG | 27 |
| mC3A | qPCR | GATGAGGACGAAGGCTGTG | 28 |
| LF82 Wzy 5 | Homologous recombination | TTAGAGAAAATTTTCCTTCAACATTAT CTACTAAAATAATAAAATCATGAgtgtag gctggagctgcttc | 29 |

TABLE 2-continued

PCR primers used in this study

| Primer | Purpose | Sequence | SEQ ID NO: |
|---|---|---|---|
| LF82 Wzy 3 | Homologous recombination | TCTCAGGTCTACCAAAGGTAGGGATAACT ATTGATACTTTAATATTCATATATATATC CTCCcatatgaatatcctcctta | 30 |
| NI1429 GT 5 | Homologous recombination | TTTTCCGTATTTATTTATACGTTGATTCT TATCCGGGGGGTACTTGCACTgtgtaggc tggagctgcttc | 31 |
| NI1429 GT 3: | Homologous recombination | GTATTACGTGAATAAAGAGTGTAGCAAAC ATCTACAACCGCTTTTTTCATACAATCCT CTTcatatgaatatcctcctta | 32 |

The chloramphenicol (Cm) resistance cassette was removed using the pCP20 plasmid except for NI1429strΔwzy::Cm. Deletion of the target gene and removal of Cm gene was confirmed by PCR using primers listed in Table 2. For complementation, the full open reading frame (ORF) of the gene was amplified from the genomic DNA of NI1429 parent strain by PCR using primers shown in Table 2. The ORF was inserted into pGEM®-T Easy by commercial TA-cloning kit (Promega, Madison, WI), followed by the transformation into the wzy mutants. The endogenous plasmid pNI1429 was isolated from NI1429 using a commercial kit (Qiagen, Hilden, Germany). The ampicillin gene was amplified from pGEM®-T Easy by using Amp5Bam and Amp3 XhoI and inserted into BamHI and XhoI sites of pNI1429 to generate pNI1429Amp. The mutant plasmid pNI1429AmpΔCol lacking the region containing colY gene, was generated by the removal of EcoRI fragments in the colY gene. The constructs pNI1429Amp and pNI1429AmpΔCol were confirmed using primer sets shown in Table 2. Strains carrying the resultant plasmids were generated by transformation of the NI1429Str with the plasmids and successive culture on L-broth plates containing 100 μg/ml ampicillin until loss of the endogenous pNI1429 and monitoring with Y5Bam/Y3XbaI. Authenticity of all plasmids was verified by DNA sequencing.

Genome sequencing and microbiota composition analyses. For genomic sequencing, genomic DNA of bacteria was isolated as described and subjected to random sequencing by Illumina MiSeq®. The resulted paired-end sequences were assembled to contigs by Velvet [52], and genes were annotated by Prokka after quality check. Ortholog gene groups and the phylogenetic tree distances of *E. coli* strains were determined by roary [54], after reannotating reference genomes, which are available in GenBank, by Prokka. For microbiota composition analysis, bacterial DNA was extracted from mouse feces using QIAamp DNA Stool Mini Kit (QIAGEN, Hilden, Germany) as instructed by the manufacturer. The V4 region of the 16S rRNA gene (252 bp) was sequenced with an Illumina MiSeq®, and analyzed by using Mothur [55, 56]. OTUs were classified into taxons at >97% identity with the use of Mothur [55]. We also used OTUs at 100% identity to determine detailed bacterial taxons by BLASTN. Spearman ranking analysis was performed using otu.association of Mothur after adding normalization for Lcn2 level and OTU abundance. Bacterial serotypes were determined using genomic sequences and SerotypeFinder (https://cge.cbs.dtu.dk/services/serotypefinder/). Phylogroups of the isolates were determined by the presence of ChuA, yjaA and TSPE4.C2 [57]. To determine the most associated co-abundance group (CAGs) with Len2 levels, logarithmic values of OTU abundance and Lcn2 level were clustered with MeV (http://www.tm4.org/) by a complete linkage method using Pearson's squared correlation coefficients. The distant tree was visualized by iTol (https://itol.embl.de/).

Adhesion and invasion assays. Adhesion and invasion assays were performed as previously described [28]. Bacteria were cultured in L-broth medium at 37° C. for 18 hours under aerobic conditions. human intestinal epithelial T84 cells were cultured for 14 days with DMEM/F12 (1:1) to polarize the cells. Polarized T84 cells were infected with the indicated strains at a multiplicity of infection (MOI) of 10 for 3 hr. For adhesion assays, cells were lysed with 0.1% Nonidet P-40 after washed with PBS and the number of bacteria associated with cells was determined by plating on L-broth. For invasion assays, cells were washed with PBS, followed by treatment with 100 g/ml of gentamicin for 1 hr to kill extracellular bacteria. Then, cells were lysed with 0.1% Nonidet P-40 and the number of internalized bacteria was determined by plating.

In vitro competition assay. For halo assays, the L-Broth agar plates were overlaid with the target bacteria strain onto 0.5% agar. Then, the formation of an inhibition zone was evaluated by spotting 3 μl of serial 1:10 dilutions of each competitor strain (starting at $OD_{600}$=1.0) followed by incubation of the plates at 37° C. overnight. For growth inhibition of LF82, LF82 and indicated strains of NI1429 were cultured at a starting $OD_{600}$ of 0.05. After 3 hr, bacteria numbers of LF82 and NI1429 strains were determined by plating on L-broth agar supplemented with 100 μg/ml ampicillin and 200 μg/ml of streptomycin, respectively.

Structural analysis of lipopolysaccharides (LPS). LPS was prepared by phenol extraction method as described [58]. A total of $2\times10^9$ bacteria were suspended with lysis buffer (100 mM SDS, 50 mM Tris-Cl, 0.128 M NaCl) and digested with 0.1 mg/ml protease K at 56° C. for 1 hr. An equal volume of TE-saturated phenol/chloroform/isoamyl alcohol (25:24:1,v/v) was added, then heated at 65° C. for 15 min. After centrifugation, LPS was precipitated by adding two volumes of ethanol to the aqueous phase and resuspended in distilled water. After electrophoresis using a 12% SDS-PAGE gel, LPS was detected with Silver Staining (Thermo Fisher Scientific).

Immunoblotting analysis. Serum levels, deposition of C3 on bacteria, and C3 processing were determined by immunoblotting using anti-C3d polyclonal antibody as described. [6] For C3 deposition assay, a total of $5\times10^8$ CFU of bacteria were incubated with 10% (v/v) indicated mouse serum for 30 min at 37° C. Unbound C3 was removed by extensive washing with ice cold PBS. Samples were boiled in Laemmli's buffer and separated by 10% SDS-PAGE (1× $10^8$ per lane). 1/100 volume of the reaction mixture was used as total protein control.

Macrophage phagocytosis and neutrophil bactericidal assays. Macrophage phagocytosis and neutrophil bactericidal assays were performed as described [6]. Macrophages were derived from bone marrow as described [59]. Macrophages were infected with the indicated bacterial strains at an MOI of 1 for 20 min with 5% fresh mouse serum and treated with 100 μg/ml of gentamicin for 1 hr before being lysed with 0.1% Nonidet P-40. The number of internalized bacteria was determined by plating. For neutrophil bactericidal assay, mouse peritoneal neutrophils were collected from the abdominal cavity of mice 6 hr after intraperitoneal injection with thioglycollate broth as described [6]. A total of 5×$10^5$ neutrophils were incubated with 5×$10^3$ bacteria with 5% fresh mouse serum for 2 hr. The number of surviving bacterial was determined by plating.

DSS-induced colitis. Mice (8 to 10-week old females) were co-housed for microbiota normalization for 2-3 weeks before treatment with 2.5 (w/v) % DSS (molecular weight 40,000-50,000; Affymetrix, Santa Clara, CA) in the drinking water for 7 days, followed by regular water for 1 day. For induction of dysbiosis, WT and $Il22^{-/-}$ mice were pretreated with an antibiotic (Abx) cocktail (ampicillin, kanamycin, gentamicin, colistin, metronidazole, and vancomycin) in the drinking water for 6 days and intraperitoneally injected with clindamycin one day before DSS treatment as described [60]. For colonization of *E. coli* strains, WT and $Il22^{-/-}$ mice were pretreated with streptomycin (2 mg/ml) in the drinking water for 1 day, then inoculated orally with 1×$10^8$ colony-forming units (CFU) of streptomycin-resistant *E. coli* before DSS treatment. For depletion of complement C3, mice were treated intraperitoneally with cobra venom factor (25 μg/body) or mock 1 day before and on day 1, 4, 7 after DSS treatment. Disease was monitored daily by measuring body weight and by collecting fecal pellets for the measurement of lipocalin 2 (Lcn2) levels and bacterial loads. On day 7, DSS was removed from drinking water and 48 hr later mice were euthanized and organs were removed for mRNA analysis and histological analysis. Blood was collected eight days after DSS treatment. Histological scores were evaluated as the sum of three parameter as follows; severity of inflammation (0, none; 1, mild; 2, moderate; 3, severe), the level of involvement (0, none; 1, mucosa, 2; mucosa and submucosa; 3, transmural), and extent of epithelial/crypt damage (0, none; 1, basal 1/3; 2, basal 2/3; 3, crypt loss; 4, crypt and surface epithelial destruction). Each score was multiplied by a factor of 1-4 [1, 0-25%; 2, 26-50%; 3, 51-75%; 4, 76-100%] according to the percentage of the colon involved [61]. Bacterial loads in feces were determined by plating on MacConkey agar plates supplemented with 200 μg/ml streptomycin. Fecal lipocalin 2 levels were determined using a commercial kit (Mouse Lipocalin 2 DuoSet ELISA, R&D Systems, Minneapolis, MN) as described [26].

mRNA quantification. Relative expression levels of gene mRNA in colon or liver were determined by quantitative RT-PCR. Colonic tissues or liver were homogenized in Trizol (Thermo Fisher Scientific) and RNA was purified using PureLink RNA Mini Kit (Thermo Fisher Scientific). cDNA was synthesized using SuperScript II Reverse Transcriptase (Thermo Fisher Scientific), and real-time PCR was performed using ABI 7900HT system (Thermo Fisher Scientific). The PCR primers used in this study are listed in Table 2. Values were normalized to gapdh levels.

Intestinal cell isolation and flow cytometric analysis. Hematopoietic cells were isolated from colonic lamina propria, as previously described [62]. Flow cytometric analysis was performed using BD FACSCelesta® (Becton Dickinson Biosciences, Franklin Lakes, NJ), and data were analyzed using FlowJo® software (Becton Dickinson Biosciences). Fluorescence-conjugated antibodies against CD11b (M1/70), CD11c (N418), MHC class II (M5/114.15.2), Ly6C (HK1.4), Ly6G (RB6-8C5), and CD45 (30F-11), were purchased from eBioscience (San Diego, CA). Neutrophil, macrophage, monocyte, and dendritic cell populations were defined by the presence of surface makers $Ly6G^+$ $MHCII^{high}CD11b^+CD45^+$, $MHCII^{high}Ly6C^+CD11b^+CD45^+$, $MHCII^{low}Ly6C^+CD11b^+CD45^+$, and $CD11c^+CD11b^-CD45^+$, respectively. The numbers of individual cell types were calculated from the percentages of detected cell types and total hematopoietic cell numbers.

Statistical analysis. Statistical analyses were performed using GraphPad® Prism software version 8 (GraphPad® Software Inc.). Difference between two groups was evaluated with two-tailed Student's t test. For multiple group comparisons, statistical analysis was performed with one-way ANOVA, followed by Tukey-Kramer's or Dunnett's post hoc test. Differences at $P<0.05$ were considered significant.

REFERENCES

The following references are herein incorporated by reference in their entireties.

1. Lebeer S, Vanderleyden J, De Keersmaecker S C. Host interactions of probiotic bacterial surface molecules: comparison with commensals and pathogens. Nat Rev Microbiol. 2010; 8(3):171-84. Epub 2010 Feb. 17. doi: 10.1038/nrmicro2297. PubMed PMID: 20157338.
2. Comstock L E, Kasper D L. Bacterial glycans: key mediators of diverse host immune responses. Cell. 2006; 126(5):847-50. doi: 10.1016/j.cell.2006.08.021. PubMed PMID: 16959564.
3. Porter N T, Martens E C. The Critical Roles of Polysaccharides in Gut Microbial Ecology and Physiology. Annu Rev Microbiol. 2017; 71:349-69. Epub 2017 Jun. 29. doi: 10.1146/annurev-micro-102215-095316. PubMed PMID: 28657886.
4. Miajlovic H, Smith S G. Bacterial self-defence: how *Escherichia coli* evades serum killing. FEMS Microbiol Lett. 2014; 354(1):1-9. doi: 10.1111/1574-6968.12419. PubMed PMID: 24617921.
5. Abreu A G, Barbosa A S. How *Escherichia coli* Circumvent Complement-Mediated Killing. Front Immunol. 2017; 8:452. Epub 2017 May 6. doi: 10.3389/fimmu.2017.00452. PubMed PMID: 28473832; PubMed Central PMCID: PMCPMC5397495.
6. Hasegawa M, Yada S, Liu M Z, Kamada N, Munoz-Planillo R, Do N, et al. Interleukin-22 regulates the complement system to promote resistance against pathobionts after pathogen-induced intestinal damage. Immunity. 2014; 41(4):620-32. doi: 10.1016/j.immuni.2014.09.010. PubMed PMID: 25367575; PubMed Central PMCID: PMCPMC4220303.
7. Poolman J T, Wacker M. Extraintestinal Pathogenic *Escherichia coli*, a Common Human Pathogen: Challenges for Vaccine Development and Progress in the Field. J Infect Dis. 2016; 213(1):6-13. Epub 2015 Sep. 4. doi: 10.1093/infdis/jiv429. PubMed PMID: 26333944; PubMed Central PMCID: PMCPMC4676548.

8. Pitout J D. Extraintestinal Pathogenic *Escherichia coli*: A Combination of Virulence with Antibiotic Resistance. Front Microbiol. 2012; 3:9. Epub 2012 Feb. 2. doi: 10.3389/fmicb.2012.00009. PubMed PMID: 22294983; PubMed Central PMCID: PMCPMC3261549.
9. Shaler C R, Elhenawy W, Coombes B K. The Unique Lifestyle of Crohn's Disease-Associated Adherent-Invasive *Escherichia coli*. J Mol Biol. 2019; 431(16):2970-81. Epub 2019 Apr. 29. doi: 10.1016/j.jmb.2019.04.023. PubMed PMID: 31029703.
10. Moriel D G, Rosini R, Seib K L, Serino L, Pizza M, Rappuoli R. *Escherichia coli*: great diversity around a common core. mBio. 2012; 3(3). Epub 2012 Jun. 7. doi: 10.1128/mBio.00118-12. PubMed PMID: 22669628; PubMed Central PMCID: PMCPMC3374390.
11. Lee J G, Han D S, Jo S V, Lee A R, Park C H, Eun C S, et al. Characteristics and pathogenic role of adherent-invasive *Escherichia coli* in inflammatory bowel disease: Potential impact on clinical outcomes. PLoS One. 2019; 14(4):e0216165. Epub 2019 Apr. 30. doi: 10.1371/journal.pone.0216165. PubMed PMID: 31034508; PubMed Central PMCID: PMCPMC6488085.
12. Palmela C, Chevarin C, Xu Z, Torres J, Sevrin G, Hirten R, et al. Adherent-invasive *Escherichia coli* in inflammatory bowel disease. Gut. 2018; 67(3):574-87. Epub 2017 Nov. 17. doi: 10.1136/gutjnl-2017-314903. PubMed PMID: 29141957.
13. Dreux N, Denizot J, Martinez-Medina M, Mellmann A, Billig M, Kisiela D, et al. Point mutations in FimH adhesin of Crohn's disease-associated adherent-invasive *Escherichia coli* enhance intestinal inflammatory response. PLoS Pathog. 2013; 9(1):e1003141. doi: 10.1371/journal.ppat. 1003141. PubMed PMID: 23358328; PubMed Central PMCID: PMCPMC3554634.
14. Bringer M A, Barnich N, Glasser A L, Bardot O, Darfeuille-Michaud A. HtrA stress protein is involved in intramacrophagic replication of adherent and invasive *Escherichia coli* strain LF82 isolated from a patient with Crohn's disease. Infect Immun. 2005; 73 (2): 712-21. Epub 2005 Jan. 25. doi: 10.1128/IAI.73.2.712-721.2005. PubMed PMID: 15664909; PubMed Central PMCID: PMCPMC546957.
15. Demarre G, Prudent V, Schenk H, Rousseau E, Bringer M A, Barnich N, et al. The Crohn's disease-associated *Escherichia coli* strain LF82 relies on SOS and stringent responses to survive, multiply and tolerate antibiotics within macrophages. PLoS Pathog. 2019; 15(11): e1008123. Epub 2019 Nov. 15. doi: 10.1371/journal.ppat.1008123. PubMed PMID: 31725806; PubMed Central PMCID: PMCPMC6855411 following competing interests: Gaelle Demarre was employed by Inovarion at the time of the study.
16. Kaser A, Zeissig S, Blumberg R S. Inflammatory bowel disease. Annu Rev Immunol. 2010; 28:573-621. doi: 10.1146/annurev-immunol-030409-101225. PubMed PMID: 20192811; PubMed Central PMCID: PMCPMC4620040.
17. Liu T C, Stappenbeck T S. Genetics and Pathogenesis of Inflammatory Bowel Disease. Annu Rev Pathol. 2016; 11:127-48. doi: 10.1146/annurev-pathol-012615-044152. PubMed PMID: 26907531; PubMed Central PMCID: PMCPMC4961083.
18. Castellanos J G, Woo V, Viladomiu M, Putzel G, Lima S, Diehl G E, et al. Microbiota-Induced TNF-like Ligand 1A Drives Group 3 Innate Lymphoid Cell-Mediated Barrier Protection and Intestinal T Cell Activation during Colitis. Immunity. 2018; 49(6):1077-89 e5. doi: 10.1016/j.immuni.2018.10.014. PubMed PMID: 30552020; PubMed Central PMCID: PMCPMC6301104.
19. Geremia A, Arancibia-Carcamo C V, Fleming M P, Rust N, Singh B, Mortensen N J, et al. IL-23-responsive innate lymphoid cells are increased in inflammatory bowel disease. J Exp Med. 2011; 208(6):1127-33. Epub 2011 May 18. doi: 10.1084/jem.20101712. PubMed PMID: 21576383; PubMed Central PMCID: PMCPMC3173242.
20. Pickert G, Neufert C, Leppkes M, Zheng Y, Wittkopf N, Warntjen M, et al. STAT3 links IL-22 signaling in intestinal epithelial cells to mucosal wound healing. J Exp Med. 2009; 206(7):1465-72. doi: 10.1084/jem.20082683. PubMed PMID: 19564350; PubMed Central PMCID: PMCPMC2715097.
21. Sakamoto K, Kim Y G, Hara H, Kamada N, Caballero-Flores G, Tolosano E, et al. IL-22 Controls Iron-Dependent Nutritional Immunity Against Systemic Bacterial Infections. Sci Immunol. 2017; 2(8). doi: 10.1126/sciimmunol.aai8371. PubMed PMID: 28286877; PubMed Central PMCID: PMCPMC5345941.
22. Baumgart M, Dogan B, Rishniw M, Weitzman G, Bosworth B, Yantiss R, et al. Culture independent analysis of ileal mucosa reveals a selective increase in invasive *Escherichia coli* of novel phylogeny relative to depletion of Clostridiales in Crohn's disease involving the ileum. ISME J. 2007; 1(5):403-18. doi: 10.1038/ismej.2007.52. PubMed PMID: 18043660.
23. Frank D N, St Amand A L, Feldman R A, Boedeker E C, Harpaz N, Pace N R. Molecular-phylogenetic characterization of microbial community imbalances in human inflammatory bowel diseases. Proc Natl Acad Sci USA. 2007; 104(34):13780-5. doi: 10.1073/pnas.0706625104. PubMed PMID: 17699621; PubMed Central PMCID: PMCPMC1959459.
24. Schmitz J M, Tonkonogy S L, Dogan B, Leblond A, Whitehead K J, Kim S C, et al. Murine Adherent and Invasive *E. coli* Induces Chronic Inflammation and Immune Responses in the Small and Large Intestines of Monoassociated IL-10−/− Mice Independent of Long Polar Fimbriae Adhesin A. Inflamm Bowel Dis. 2019; 25(5):875-85. Epub 2018 Dec. 24. doi: 10.1093/ibd/izy386. PubMed PMID: 30576451; PubMed Central PMCID: PMCPMC6458545.
25. Sabat R, Ouyang W, Wolk K. Therapeutic opportunities of the IL-22-IL-22R1 system. Nat Rev Drug Discov. 2014; 13(1):21-38. doi: 10.1038/nrd4176. PubMed PMID: 24378801.
26. Chassaing B, Srinivasan G, Delgado M A, Young A N, Gewirtz A T, Vijay-Kumar M. Fecal lipocalin 2, a sensitive and broadly dynamic non-invasive biomarker for intestinal inflammation. PLoS One. 2012; 7(9):e44328. doi: 10.1371/journal.pone.0044328. PubMed PMID: 22957064; PubMed Central PMCID: PMCPMC3434182.
27. Hasegawa M, Kamada N, Jiao Y, Liu M Z, Nunez G, Inohara N. Protective role of commensals against *Clostridium difficile* infection via an IL-1beta-mediated positive-feedback loop. J Immunol. 2012; 189(6):3085-91. doi: 10.4049/jimmunol. 1200821. PubMed PMID: 22888139; PubMed Central PMCID: PMCPMC3752782.
28. Darfeuille-Michaud A, Boudeau J, Bulois P, Neut C, Glasser A L, Barnich N, et al. High prevalence of adherent-invasive *Escherichia coli* associated with ileal mucosa in Crohn's disease. Gastroenterology. 2004; 127 (2):412-21. PubMed PMID: 15300573.
29. Nedialkova L P, Denzler R, Koeppel M B, Diehl M, Ring D, Wille T, et al. Inflammation fuels colicin Ib-dependent competition of *Salmonella* serovar *Typhimurium* and *E.*

*coli* in enterobacterial blooms. PLoS Pathog. 2014; 10(1): e1003844. doi: 10.1371/journal.ppat. 1003844. PubMed PMID: 24391500; PubMed Central PMCID: PMCPMC3879352.

30. Whitfield C. Biosynthesis and assembly of capsular polysaccharides in *Escherichia coli*. Annu Rev Biochem. 2006; 75:39-68. doi: 10.1146/annurev.biochem.75.103004.142545. PubMed PMID: 16756484.

31. Woodward R, Yi W, Li L, Zhao G, Eguchi H, Sridhar P R, et al. In vitro bacterial polysaccharide biosynthesis: defining the functions of wzy and Wzz. Nat Chem Biol. 2010; 6(6):418-23. doi: 10.1038/nchembio.351. PubMed PMID: 20418877; PubMed Central PMCID: PMCPMC2921718.

32. Grozdanov L, Zahringer U, Blum-Oehler G, Brade L, Henne A, Knirel Y A, et al. A single nucleotide exchange in the wzy gene is responsible for the semirough O6 lipopolysaccharide phenotype and serum sensitivity of *Escherichia coli* strain Nissle 1917. J Bacteriol. 2002; 184(21):5912-25. doi: 10.1128/jb.184.21.5912-5925.2002. PubMed PMID: 12374825; PubMed Central PMCID: PMCPMC135379.

33. Guo H, Yi W, Shao J, Lu Y, Zhang W, Song J, et al. Molecular analysis of the O-antigen gene cluster of *Escherichia coli* O86:B7 and characterization of the chain length determinant gene (wzz). Appl Environ Microbiol. 2005; 71(12):7995-8001. Epub 2005 Dec. 8. doi: 10.1128/AEM.71.12.7995-8001.2005. PubMed PMID: 16332778; PubMed Central PMCID: PMCPMC1317457.

34. Oberholzer J, Yu D, Triponez F, Cretin N, Andereggen E, Mentha G, et al. Decomplementation with cobra venom factor prolongs survival of xenografted islets in a rat to mouse model. Immunology. 1999; 97(1):173-80. doi: 10.1046/j.1365-2567.1999.00742.x. PubMed PMID: 10447729; PubMed Central PMCID: PMCPMC2326800.

35. Anderson M T, Mitchell L A, Zhao L, Mobley H L T. Capsule Production and Glucose Metabolism Dictate Fitness during *Serratia marcescens* Bacteremia. MBio. 2017; 8(3). doi: 10.1128/mBio.00740-17. PubMed PMID: 28536292; PubMed Central PMCID: PMCPMC5442460.

36. de Vries S P, Gupta S, Baig A, Wright E, Wedley A, Jensen A N, et al. Genome-wide fitness analyses of the foodborne pathogen *Campylobacter jejuni* in in vitro and in vivo models. Sci Rep. 2017; 7(1):1251. doi: 10.1038/s41598-017-01133-4. PubMed PMID: 28455506; PubMed Central PMCID: PMCPMC5430854.

37. Buckles E L, Wang X, Lane M C, Lockatell C V, Johnson D E, Rasko D A, et al. Role of the K2 capsule in *Escherichia coli* urinary tract infection and serum resistance. J Infect Dis. 2009; 199(11):1689-97. doi: 10.1086/598524. PubMed PMID: 19432551; PubMed Central PMCID: PMCPMC3872369.

38. Sachdeva S, Palur R V, Sudhakar K U, Rathinavelan T. *E. coli* Group 1 Capsular Polysaccharide Exportation Nanomachinary as a Plausible Antivirulence Target in the Perspective of Emerging Antimicrobial Resistance. Front Microbiol. 2017; 8:70. doi: 10.3389/fmicb.2017.00070. PubMed PMID: 28217109; PubMed Central PMCID: PMCPMC5290995.

39. Sarkar S, Ulett G C, Totsika M, Phan M D, Schembri M A. Role of capsule and O antigen in the virulence of uropathogenic *Escherichia coli*. PLoS One. 2014; 9(4): e94786. doi: 10.1371/journal.pone.0094786. PubMed PMID: 24722484; PubMed Central PMCID: PMCPMC3983267.

40. Sassone-Corsi M, Nuccio S P, Liu H, Hernandez D, Vu C T, Takahashi A A, et al. Microcins mediate competition among Enterobacteriaceae in the inflamed gut. Nature. 2016; 540(7632):280-3. doi: 10.1038/nature20557. PubMed PMID: 27798599; PubMed Central PMCID: PMCPMC5145735.

41. Patzer S I, Baquero M R, Bravo D, Moreno F, Hantke K. The colicin G, H and X determinants encode microcins M and H47, which might utilize the catecholate siderophore receptors FepA, Cir, Fiu and IroN. Microbiology. 2003; 149(Pt 9):2557-70. Epub 2003 Sep. 2. doi: 10.1099/mic.0.26396-0. PubMed PMID: 12949180.

42. Hancock V, Dahl M, Klemm P. Probiotic *Escherichia coli* strain Nissle 1917 outcompetes intestinal pathogens during biofilm formation. J Med Microbiol. 2010; 59(Pt 4):392-9. Epub 2010 Jan. 30. doi: 10.1099/jmm.0.008672-0. PubMed PMID: 20110388.

43. Massip C, Branchu P, Bossuet-Greif N, Chagneau C V, Gaillard D, Martin P, et al. Deciphering the interplay between the genotoxic and probiotic activities of *Escherichia coli* Nissle 1917. PLoS Pathog. 2019; 15(9): e1008029. Epub 2019 Sep. 24. doi: 10.1371/journal.ppat.1008029. PubMed PMID: 31545853; PubMed Central PMCID: PMCPMC6776366.

44. Fang K, Jin X, Hong S H. Probiotic *Escherichia coli* inhibits biofilm formation of pathogenic *E. coli* via extracellular activity of DegP. Sci Rep. 2018; 8(1):4939. Epub 2018 Mar. 23. doi: 10.1038/s41598-018-23180-1. PubMed PMID: 29563542; PubMed Central PMCID: PMCPMC5862908.

45. Sorbara M T, Foerster E G, Tsalikis J, Abdel-Nour M, Mangiapane J, Sirluck-Schroeder I, et al. Complement C3 Drives Autophagy-Dependent Restriction of Cyto-invasive Bacteria. Cell Host Microbe. 2018; 23(5):644-52 e5. Epub 2018 May 11. doi: 10.1016/j.chom.2018.04.008. PubMed PMID: 29746835.

46. Sunderhauf A, Skibbe K, Preisker S, Ebbert K, Verschoor A, Karsten C M, et al. Regulation of epithelial cell expressed C3 in the intestine—Relevance for the pathophysiology of inflammatory bowel disease? Mol Immunol. 2017; 90:227-38. Epub 2017 Aug. 28. doi: 10.1016/j.molimm.2017.08.003. PubMed PMID: 28843904.

47. Bernstein C N. Treatment of IBD: where we are and where we are going. Am J Gastroenterol. 2015; 110(1): 114-26. doi: 10.1038/ajg.2014.357. PubMed PMID: 25488896.

48. Kruis W, Fric P, Pokrotnieks J, Lukas M, Fixa B, Kascak M, et al. Maintaining remission of ulcerative colitis with the probiotic *Escherichia coli* Nissle 1917 is as effective as with standard mesalazine. Gut. 2004; 53(11):1617-23. doi: 10.1136/gut.2003.037747. PubMed PMID: 15479682; PubMed Central PMCID: PMCPMC1774300.

49. Newcombe H B, Mc G J. On the nonadaptive nature of change to full streptomycin resistance in *Escherichia coli*. J Bacteriol. 1951; 62(5):539-44. PubMed PMID: 14897828; PubMed Central PMCID: PMCPMC386167.

50. Datsenko K A, Wanner B L. One-step inactivation of chromosomal genes in *Escherichia coli* K-12 using PCR products. Proc Natl Acad Sci USA. 2000; 97(12):6640-5. doi: 10.1073/pnas. 120163297. PubMed PMID: 10829079; PubMed Central PMCID: PMCPMC18686.

51. Charles T C, Nester E W. A chromosomally encoded two-component sensory transduction system is required for virulence of *Agrobacterium tumefaciens*. J Bacteriol. 1993; 175(20):6614-25. doi: 10.1128/jb.175.20.6614-6625.1993. PubMed PMID: 8407839; PubMed Central PMCID: PMCPMC206773.

52. Zerbino D R, Birney E. Velvet: algorithms for de novo short read assembly using de Bruijn graphs. Genome Res. 2008; 18(5):821-9. Epub 2008 Mar. 20. doi: 10.1101/gr.074492.107. PubMed PMID: 18349386; PubMed Central PMCID: PMCPMC2336801.
53. Seemann T. Prokka: rapid prokaryotic genome annotation. Bioinformatics. 2014; 30(14):2068-9. Epub 2014 Mar. 20. doi: 10.1093/bioinformatics/btu153. PubMed PMID: 24642063.
54. Page A J, Cummins C A, Hunt M, Wong V K, Reuter S, Holden M T, et al. Roary: rapid large-scale prokaryote pan genome analysis. Bioinformatics. 2015; 31(22):3691-3. Epub 2015 Jul. 23. doi: 10.1093/bioinformatics/btv421. PubMed PMID: 26198102; PubMed Central PMCID: PMCPMC4817141.
55. Schloss P D, Westcott S L, Ryabin T, Hall J R, Hartmann M, Hollister E B, et al. Introducing mothur: open-source, platform-independent, community-supported software for describing and comparing microbial communities. Appl Environ Microbiol. 2009; 75(23):7537-41. doi: 10.1128/AEM.01541-09. PubMed PMID: 19801464; PubMed Central PMCID: PMCPMC2786419.
56. Kozich J J, Westcott S L, Baxter N T, Highlander S K, Schloss P D. Development of a dual-index sequencing strategy and curation pipeline for analyzing amplicon sequence data on the MiSeq® Illumina sequencing platform. Appl Environ Microbiol. 2013; 79(17):5112-20. doi: 10.1128/AEM.01043-13. PubMed PMID: 23793624; PubMed Central PMCID: PMCPMC3753973.
57. Clermont O, Bonacorsi S, Bingen E. Rapid and simple determination of the *Escherichia coli* phylogenetic group. Appl Environ Microbiol. 2000; 66(10):4555-8. Epub 2000 Sep. 30. doi: 10.1128/aem.66.10.4555-4558.2000. PubMed PMID: 11010916; PubMed Central PMCID: PMCPMC92342.
58. Kenyon J J, Reeves P R. The wzy O-antigen polymerase of *Yersinia pseudotuberculosis* O:2a has a dependence on the Wzz chain-length determinant for efficient polymerization. FEMS Microbiol Lett. 2013; 349(2):163-70. doi: 10.1111/1574-6968.12311. PubMed PMID: 24164168.
59. Franchi L, Munoz-Planillo R, Nunez G. Sensing and reacting to microbes through the inflammasomes. Nat Immunol. 2012; 13(4):325-32. doi: 10.1038/ni.2231. PubMed PMID: 22430785; PubMed Central PMCID: PMCPMC3449002.
60. Hasegawa M, Yamazaki T, Kamada N, Tawaratsumida K, Kim Y G, Nunez G, et al. Nucleotide-binding oligomerization domain 1 mediates recognition of *Clostridium difficile* and induces neutrophil recruitment and protection against the pathogen. J Immunol. 2011; 186(8):4872-80. doi: 10.4049/jimmunol. 1003761. PubMed PMID: 21411735.
61. Seo S U, Kamada N, Munoz-Planillo R, Kim Y G, Kim D, Koizumi Y, et al. Distinct Commensals Induce Interleukin-1beta via NLRP3 Inflammasome in Inflammatory Monocytes to Promote Intestinal Inflammation in Response to Injury. Immunity. 2015; 42(4):744-55. doi: 10.1016/j.immuni.2015.03.004. PubMed PMID: 25862092; PubMed Central PMCID: PMCPMC4408263.
62. Hayashi A, Sato T, Kamada N, Mikami Y, Matsuoka K, Hisamatsu T, et al. A single strain of *Clostridium butyricum* induces intestinal IL-10-producing macrophages to suppress acute experimental colitis in mice. Cell Host Microbe. 2013; 13(6):711-22. doi: 10.1016/j.chom.2013.05.013. PubMed PMID: 23768495.
63. Datsenko K A, Wanner B L. One-step inactivation of chromosomal genes in *Escherichia coli* K-12 using PCR products. Proc Natl Acad Sci USA 2000; 6(97):6640-5. doi: 10.1073/pnas. 120163297.
64. Hasegawa M, Yada S, Liu M Z, Kamada N, Munoz-Planillo R, Do N, Nunex G, Inohara N. Interleukin-22 regulates the complement system to promote resistance against pathobionts after pathogen-induced intestinal damage. Immunity 2014; 10(41):620-32. doi: 10.1016/j.immuni.2014.09.010.

The invention claimed is:

1. A method of treating or ameliorating intestinal inflammation in a subject, comprising administering to said subject a therapeutically effective amount of a modified adherent-invasive *E. coli* (AIEC) wherein said modified AIEC comprises an inactivated lipopolysaccharide O polymerase (wzy) gene and a pharmaceutically acceptable carrier.

2. The method of claim 1, wherein said modified AIEC has greater sensitivity to the complement system than an unmodified AIEC bacteria.

3. The method of claim 1, wherein said modified AIEC has greater susceptibility to engulfment and/or killing by phagocytes than an unmodified AIEC while retaining its ability to outcompete unmodified AIEC bacteria.

4. The method of claim 1, wherein said intestinal inflammation is colitis, chemically-induced colitis, antibiotically-induced colitis, irritable bowel disease, inflammatory bowel disease, Crohn's disease, and/or ulcerative colitis.

5. The method of claim 1, wherein said administering is oral, rectal or parenteral administering.

6. The method of claim 1, wherein said subject is immunocompromised.

7. The method of claim 1, wherein said modified AIEC is administered in combination with an antibiotic drug, an anti-diarrheal drug, a laxative drug, a vitamin, a non-steroidal anti-inflammatory drug, a steroidal anti-inflammatory drug, an immune suppressor drug, and/or a biologic therapy.

8. The method of claim 1, wherein said modified AIEC is administered in combination with a complement C3 agonist, a colicin antagonist, and/or an anti-C3 inhibitor.

9. The method of claim 1, further comprising testing said subject for the presence, absence, or amount of AIEC in the gut microbiota.

10. The method of claim 1 wherein said inactivated wzy gene is a deleted wzy gene.

* * * * *

SEQUENCE LISTING

```
<160> NUMBER OF SEQ ID NOS: 32

<210> SEQ ID NO 1
<211> LENGTH: 70
<212> TYPE: DNA
<213> ORGANISM: Artificial sequence
<220> FEATURE:
<223> OTHER INFORMATION: Synthetic

<400> SEQUENCE: 1

aaaaaaatgc ttatggtcag tacttaatca aattgacaca gggataataa gtgtaggctg     60

gagctgcttc                                                            70


<210> SEQ ID NO 2
<211> LENGTH: 69
<212> TYPE: DNA
<213> ORGANISM: Artificial sequence
<220> FEATURE:
<223> OTHER INFORMATION: Synthetic

<400> SEQUENCE: 2

ttctgaggta gatctccgtt atagacactc ataataacag ctatcttgtc catatgaata     60

tcctcctta                                                             69
```

<210> SEQ ID NO 3
<211> LENGTH: 73
<212> TYPE: DNA
<213> ORGANISM: Artificial sequence
<220> FEATURE:
<223> OTHER INFORMATION: Synthetic

<400> SEQUENCE: 3
acagctgaac ccgaagagat gattgtaatg aaacgagtta ttaccctgtt tgctgtaggc 60
tggagctgct tcg 73

<210> SEQ ID NO 4
<211> LENGTH: 74
<212> TYPE: DNA
<213> ORGANISM: Artificial sequence
<220> FEATURE:
<223> OTHER INFORMATION: Synthetic

<400> SEQUENCE: 4
cagcattagc aatgtcctgt gatttcttta ttgataaaca aaagtcacgc caatcatatg 60
aatatcctcc ttag 74

<210> SEQ ID NO 5
<211> LENGTH: 20
<212> TYPE: DNA
<213> ORGANISM: Artificial sequence
<220> FEATURE:
<223> OTHER INFORMATION: Synthetic

<400> SEQUENCE: 5
aattgaagag cgtcaggggc 20

<210> SEQ ID NO 6
<211> LENGTH: 20
<212> TYPE: DNA
<213> ORGANISM: Artificial sequence
<220> FEATURE:
<223> OTHER INFORMATION: Synthetic

<400> SEQUENCE: 6
gttgccagtg cttgccttac 20

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7
ggcaatgaaa gacggtgagc 20

<210> SEQ ID NO 8
<211> LENGTH: 22
<212> TYPE: DNA
<213> ORGANISM: Artificial sequence
<220> FEATURE:
<223> OTHER INFORMATION: Synthetic

<400> SEQUENCE: 8
cattcaggca gtgattagca tc 22

<210> SEQ ID NO 9
<211> LENGTH: 20
<212> TYPE: DNA

<213> ORGANISM: Artificial sequence
<220> FEATURE:
<223> OTHER INFORMATION: Synthetic

<400> SEQUENCE: 9
gataacacgc cgccataagc 20

<210> SEQ ID NO 10
<211> LENGTH: 20
<212> TYPE: DNA
<213> ORGANISM: Artificial sequence
<220> FEATURE:
<223> OTHER INFORMATION: Synthetic

<400> SEQUENCE: 10
ggcgtgttac ggtgaaaacc 20

<210> SEQ ID NO 11
<211> LENGTH: 30
<212> TYPE: DNA
<213> ORGANISM: Artificial sequence
<220> FEATURE:
<223> OTHER INFORMATION: Synthetic

<400> SEQUENCE: 11
tgatatcagg gataataaat ggaatctcta 30

<210> SEQ ID NO 12
<211> LENGTH: 31
<212> TYPE: DNA
<213> ORGANISM: Artificial sequence
<220> FEATURE:
<223> OTHER INFORMATION: Synthetic

<400> SEQUENCE: 12
gtcgacttat acctcggtat ctaaataaat g 31

<210> SEQ ID NO 13
<211> LENGTH: 27
<212> TYPE: DNA
<213> ORGANISM: Artificial sequence
<220> FEATURE:
<223> OTHER INFORMATION: Synthetic

<400> SEQUENCE: 13
ggggatccgg agatctcccg atccgtc 27

<210> SEQ ID NO 14
<211> LENGTH: 33
<212> TYPE: DNA
<213> ORGANISM: Artificial sequence
<220> FEATURE:
<223> OTHER INFORMATION: Synthetic

<400> SEQUENCE: 14
ccgggaattc tagaagatcc tttgatcttt tct 33

<210> SEQ ID NO 15
<211> LENGTH: 28
<212> TYPE: DNA
<213> ORGANISM: Artificial sequence
<220> FEATURE:
<223> OTHER INFORMATION: Synthetic

<400> SEQUENCE: 15
aaggatcctg gtgttggtca cctctgga 28

<210> SEQ ID NO 16
<211> LENGTH: 31
<212> TYPE: DNA
<213> ORGANISM: Artificial sequence
<220> FEATURE:
<223> OTHER INFORMATION: Synthetic

<400> SEQUENCE: 16
aacccgggtc tagattcgct gtgtccacat c 31

<210> SEQ ID NO 17
<211> LENGTH: 28
<212> TYPE: DNA
<213> ORGANISM: Artificial sequence
<220> FEATURE:
<223> OTHER INFORMATION: Synthetic

<400> SEQUENCE: 17
gcttctgtca ataaactgat ggctaatc 28

<210> SEQ ID NO 18
<211> LENGTH: 28
<212> TYPE: DNA
<213> ORGANISM: Artificial sequence
<220> FEATURE:
<223> OTHER INFORMATION: Synthetic

<400> SEQUENCE: 18
aaacttattc cccatatcct ctgcatca 28

<210> SEQ ID NO 19
<211> LENGTH: 21
<212> TYPE: DNA
<213> ORGANISM: Artificial sequence
<220> FEATURE:
<223> OTHER INFORMATION: Synthetic

<400> SEQUENCE: 19
actcctacgg gaggcagcag t 21

<210> SEQ ID NO 20
<211> LENGTH: 18
<212> TYPE: DNA
<213> ORGANISM: Artificial sequence
<220> FEATURE:
<223> OTHER INFORMATION: Synthetic

<400> SEQUENCE: 20
attaccgcgg ctgctggc 18

<210> SEQ ID NO 21
<211> LENGTH: 25
<212> TYPE: DNA
<213> ORGANISM: Artificial sequence
<220> FEATURE:
<223> OTHER INFORMATION: Synthetic

<400> SEQUENCE: 21
cattgacgtt acccgcagaa gaagc 25

<210> SEQ ID NO 22
<211> LENGTH: 21
<212> TYPE: DNA
<213> ORGANISM: Artificial sequence
<220> FEATURE:

<223> OTHER INFORMATION: Synthetic

<400> SEQUENCE: 22
ctctacgaga ctcaagcttg c 21

<210> SEQ ID NO 23
<211> LENGTH: 20
<212> TYPE: DNA
<213> ORGANISM: Artificial sequence
<220> FEATURE:
<223> OTHER INFORMATION: Synthetic

<400> SEQUENCE: 23
cccttaagag ggatgctgcc 20

<210> SEQ ID NO 24
<211> LENGTH: 20
<212> TYPE: DNA
<213> ORGANISM: Artificial sequence
<220> FEATURE:
<223> OTHER INFORMATION: Synthetic

<400> SEQUENCE: 24
tacggccaaa tccgttcaca 20

<210> SEQ ID NO 25
<211> LENGTH: 20
<212> TYPE: DNA
<213> ORGANISM: Artificial sequence
<220> FEATURE:
<223> OTHER INFORMATION: Synthetic

<400> SEQUENCE: 25
gctcagctcc tgtcacatca 20

<210> SEQ ID NO 26
<211> LENGTH: 20
<212> TYPE: DNA
<213> ORGANISM: Artificial sequence
<220> FEATURE:
<223> OTHER INFORMATION: Synthetic

<400> SEQUENCE: 26
agcttcttct cgctcagacg 20

<210> SEQ ID NO 27
<211> LENGTH: 23
<212> TYPE: DNA
<213> ORGANISM: Artificial sequence
<220> FEATURE:
<223> OTHER INFORMATION: Synthetic

<400> SEQUENCE: 27
gggctgttaa atggttgatt ctg 23

<210> SEQ ID NO 28
<211> LENGTH: 19
<212> TYPE: DNA
<213> ORGANISM: Artificial sequence
<220> FEATURE:
<223> OTHER INFORMATION: Synthetic

<400> SEQUENCE: 28
gatgaggacg aaggctgtg 19

-continued

```
<210> SEQ ID NO 29
<211> LENGTH: 70
<212> TYPE: DNA
<213> ORGANISM: Artificial sequence
<220> FEATURE:
<223> OTHER INFORMATION: Synthetic

<400> SEQUENCE: 29

ttagagaaaa ttttccttca acattatcta ctaaaataat aaaatcatga gtgtaggctg     60

gagctgcttc                                                            70


<210> SEQ ID NO 30
<211> LENGTH: 81
<212> TYPE: DNA
<213> ORGANISM: Artificial sequence
<220> FEATURE:
<223> OTHER INFORMATION: Synthetic

<400> SEQUENCE: 30

tctcaggtct accaaaggta gggataacta ttgatacttt aatattcata tatatatcct     60

cccatatgaa tatcctcctt a                                               81


<210> SEQ ID NO 31
<211> LENGTH: 70
<212> TYPE: DNA
<213> ORGANISM: Artificial sequence
<220> FEATURE:
<223> OTHER INFORMATION: Synthetic

<400> SEQUENCE: 31

ttttccgtat ttatttatac gttgattctt atccgggggg tacttgcact gtgtaggctg     60

gagctgcttc                                                            70


<210> SEQ ID NO 32
<211> LENGTH: 80
<212> TYPE: DNA
<213> ORGANISM: Artificial sequence
<220> FEATURE:
<223> OTHER INFORMATION: Synthetic

<400> SEQUENCE: 32

gtattacgtg aataaagagt gtagcaaaca tctacaaccg ctttttttcat acaatcctct     60

tcatatgaat atcctcctta                                                 80
```